United States Patent [19]

Haber et al.

[11] Patent Number: 5,275,614
[45] Date of Patent: Jan. 4, 1994

[54] AXIALLY EXTENDABLE ENDOSCOPIC SURGICAL INSTRUMENT

[75] Inventors: Terry M. Haber, Lake Forest; William H. Smedley, Lake Elsinore; Clark B. Foster, Laguna Niguel, all of Calif.

[73] Assignee: Habley Medical Technology Corporation, Laguna Hills, Calif.

[21] Appl. No.: 898,101

[22] Filed: Jun. 12, 1992

Related U.S. Application Data

[63] Continuation-in-part of Ser. No. 839,510, Feb. 21, 1992, Ser. No. 850,674, Mar. 13, 1992, and Ser. No. 878,957, May 4, 1992.

[51] Int. Cl.$^5$ .............................................. A61B 17/00
[52] U.S. Cl. ..................................... 606/207; 606/139; 606/144; 606/206; 606/208
[58] Field of Search ................. 606/205-207, 142, 143, 139, 144, 145

[56] References Cited

U.S. PATENT DOCUMENTS

| | | | |
|---|---|---|---|
| 1,274,669 | 8/1918 | Bohn . | |
| 2,363,334 | 11/1944 | Jones . | |
| 2,365,647 | 12/1944 | Ogburn . | |
| 3,168,097 | 2/1965 | Dormia . | |
| 4,152,920 | 5/1979 | Green | 606/143 |
| 4,562,839 | 1/1986 | Blake, III et al. | 606/143 |
| 4,580,567 | 4/1986 | Schweitzer et al. . | |
| 4,643,190 | 2/1987 | Heimberger . | |
| 4,706,668 | 11/1987 | Backer | 606/142 |
| 4,760,848 | 8/1988 | Hasson | 606/206 |
| 4,815,476 | 3/1989 | Clossick . | |
| 4,872,456 | 10/1989 | Hasson . | |
| 4,890,615 | 1/1990 | Caspari et al. . | |
| 4,950,273 | 8/1990 | Briggs | 606/205 |
| 5,084,054 | 1/1992 | Bencini et al. . | |
| 5,147,373 | 9/1992 | Ferzli | 606/206 |
| 5,174,300 | 12/1992 | Bales et al. | 606/139 |

FOREIGN PATENT DOCUMENTS 2044108 10/1980 United Kingdom ................ 606/142

OTHER PUBLICATIONS

Jarit Laparoscopic Cholecystectomy Instruments, Star 2000 Series, 1991.

*Primary Examiner*—Stephen C. Pellegrino
*Assistant Examiner*—Jeffrey A. Schmidt
*Attorney, Agent, or Firm*—Townsend and Townsend Khourie and Crew

[57] ABSTRACT

An endoscopic surgical instrument is designed for axial elongation by incorporating a manually operated mechanism which elongates the instrument upon manual rotation. The manually operated mechanism is joined to and supports a functional element at the tip of the instrument. Operation of the functional element at the distal tip of the instrument is achieved by manipulations at the proximal end of the instrument, and is not impaired by the extension. The user can lock the tip against rotary motion. The tip assembly is removably attached to the instrument, such as by using a bayonet-type locking element.

21 Claims, 22 Drawing Sheets

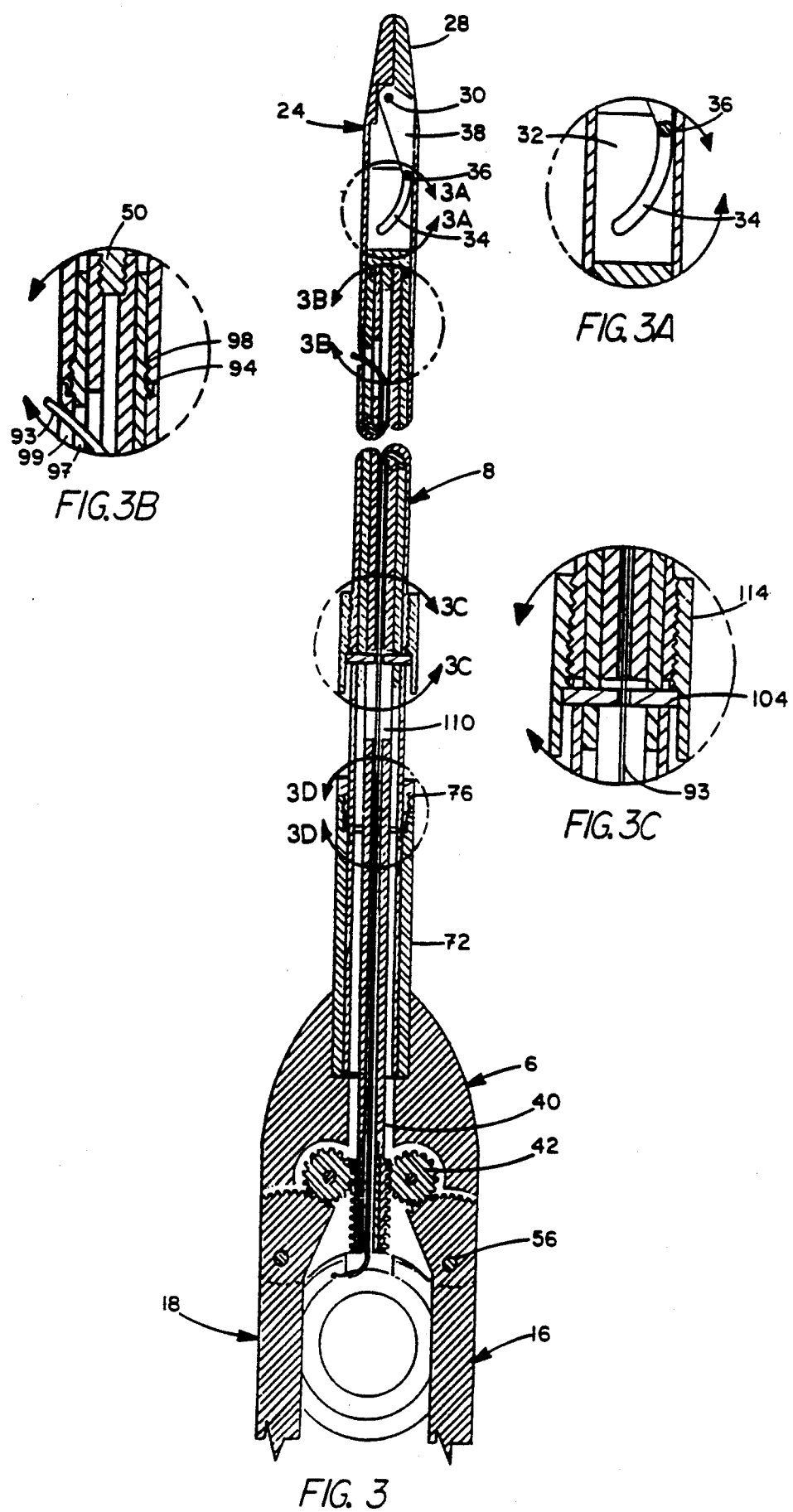

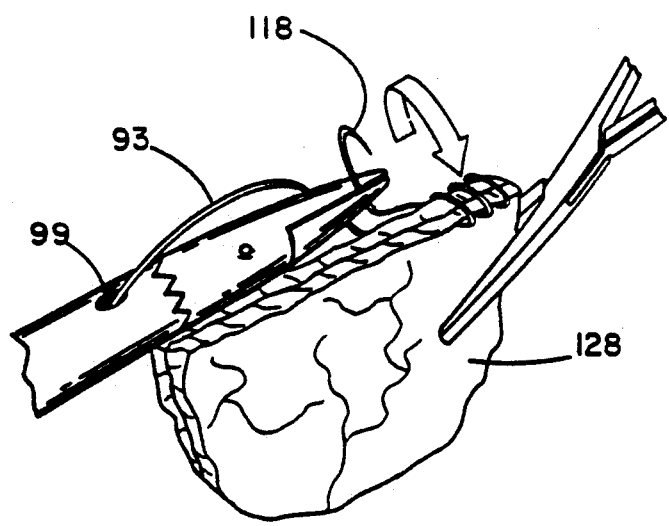
FIG. 6
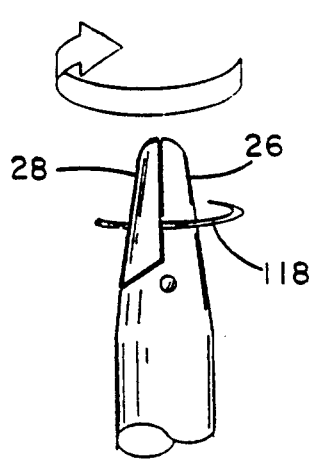 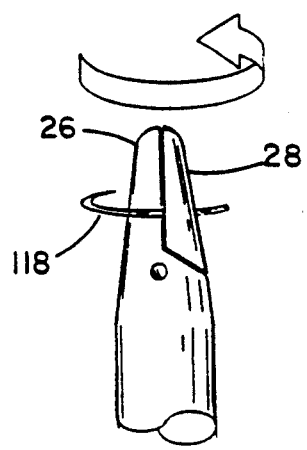
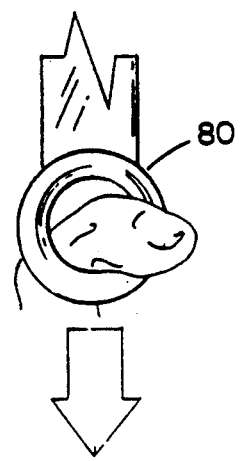 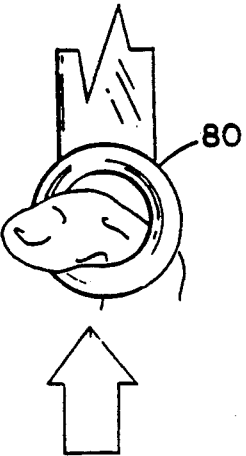
FIG. 6A　　　　　　　　FIG.6B

AXIALLY EXTENDABLE ENDOSCOPIC SURGICAL INSTRUMENT

CROSS REFERENCE TO RELATED APPLICATIONS

This is continuation-in-part of the following U.S. patent applications, the disclosures of which are incorporated by reference: application Ser. No. 07/839,510, filed Feb. 21, 1992 for Needle Manipulator; application Ser. No. 07/850,674, filed Mar. 13, 1992 for Endoscopic Surgical Instrument; application Ser. No. 07/878,957, filed May 4, 1992 for Axially Extendable Endoscopic Surgical Instrument.

BACKGROUND OF THE INVENTION

The practice of endoscopic or minimally-invasive surgery is becoming more widely used because it is less traumatic than conventional open surgery, thus reducing hospitalization times and costs as well as minimizing patient discomfort. With endoscopic surgery, only a relatively tiny incision is necessary, with the instrument being passed through this incision. A tissue-protective port is sometimes used to minimize tissue trauma on the walls of the incision. Various types of endoscopic instruments are passed through the small incision and appropriate surgical procedures are carried out.

One type of endoscopic instrument is forceps having tips specially configured to grasp, manipulate or cut tissue. Conventional forceps typically use scissors type of thumb and finger rings. Such forceps, although well designed for cutting and simple grasping tasks for open surgical procedures, are unwieldy for certain minimally-invasive surgical tasks, such as placing sutures during endoscopic procedures; conventional forceps require the physician to reposition the entire instrument to adjust the radial orientation of the tip.

SUMMARY OF THE INVENTION

The present invention is directed to a minimally-invasive surgical instrument which permits the physician to axially increase or decrease the length of the instrument at any time, while retaining full function and precise control of the tip assembly. The physician can also independently actuate the tip and rotate the tip through non-rotational, planar manipulation of the handle control assembly. This is accomplished without requiring the physician to rotate his or her wrist.

The extension/retraction capability of the instrument is achieved by a combination of two extension mechanisms, each containing a rod and a tube to receive the rod, the tube and rod mated by threads so that axial extension is achieved by rotating the tube relative to the rod or the rod relative to the tube. In preferred embodiments of the invention, the two mechanisms are positioned one inside the other, so that the rod of the outer mechanism is hollow and receives the tube and rod of the inner mechanism. The two mechanisms are functionally linked together so that extension of one produces extension of the other.

Other features and advantages of the invention will be evident from the following description in which the preferred embodiments have been set forth in detail in conjunction with the accompanying drawings.

BRIEF DESCRIPTION OF THE DRAWINGS

FIG. 3 is a cross-sectional view of a portion of the needle manipulator of FIG. 1 with the jaws in a closed position;

FIGS. 3A–3D show portions of the needle manipulator of FIG. 3 enlarged to show detail;

FIG. 6 is an enlarged view of the tip assembly of FIG. 1 shown manipulating a needle to suture tissue;

FIGS. 6A and 6B illustrate the rotary movement of the tip assembly and needle of FIG. 6 as the trigger is pulled and pushed, respectively;

DESCRIPTION OF THE PREFERRED EMBODIMENTS

Figure 1:
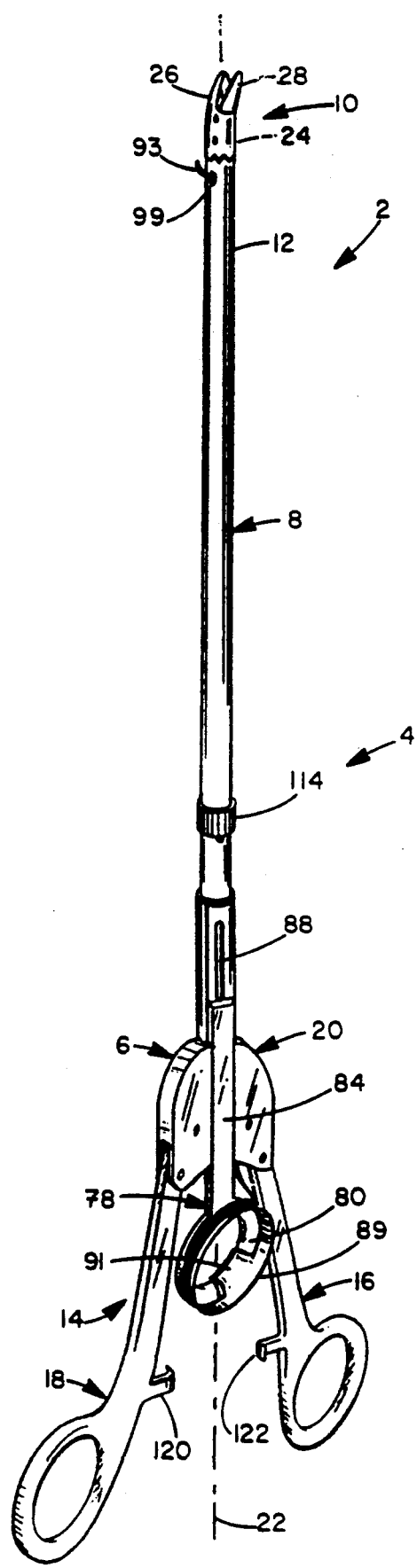
FIG. 1 is an overall perspective view of a needle manipulator type of endoscopic surgical instrument.

FIG. 1 illustrates a rotational tip needle manipulator type of endoscopic surgical instrument. Needle manipulator 2 includes an elongate body 4, the body including a base 6 and an elongate tip carrier tube 8. Manipulator 2 also includes a tip assembly 10 mounted to the distal end 12 of tube 8 and a jaw driver assembly 14. Jaw driver assembly 14 is used to manipulate the jaws carried by the tip assembly as is described below through the opening and closing of jaw actuating finger and thumb loops 16, 18. Manipulator 2 further includes a jaw rotator assembly 20 used to rotate tip carrier tube 8 and tip assembly 10 therewith about the longitudinal axis 22 of the manipulator.

Figure 2:
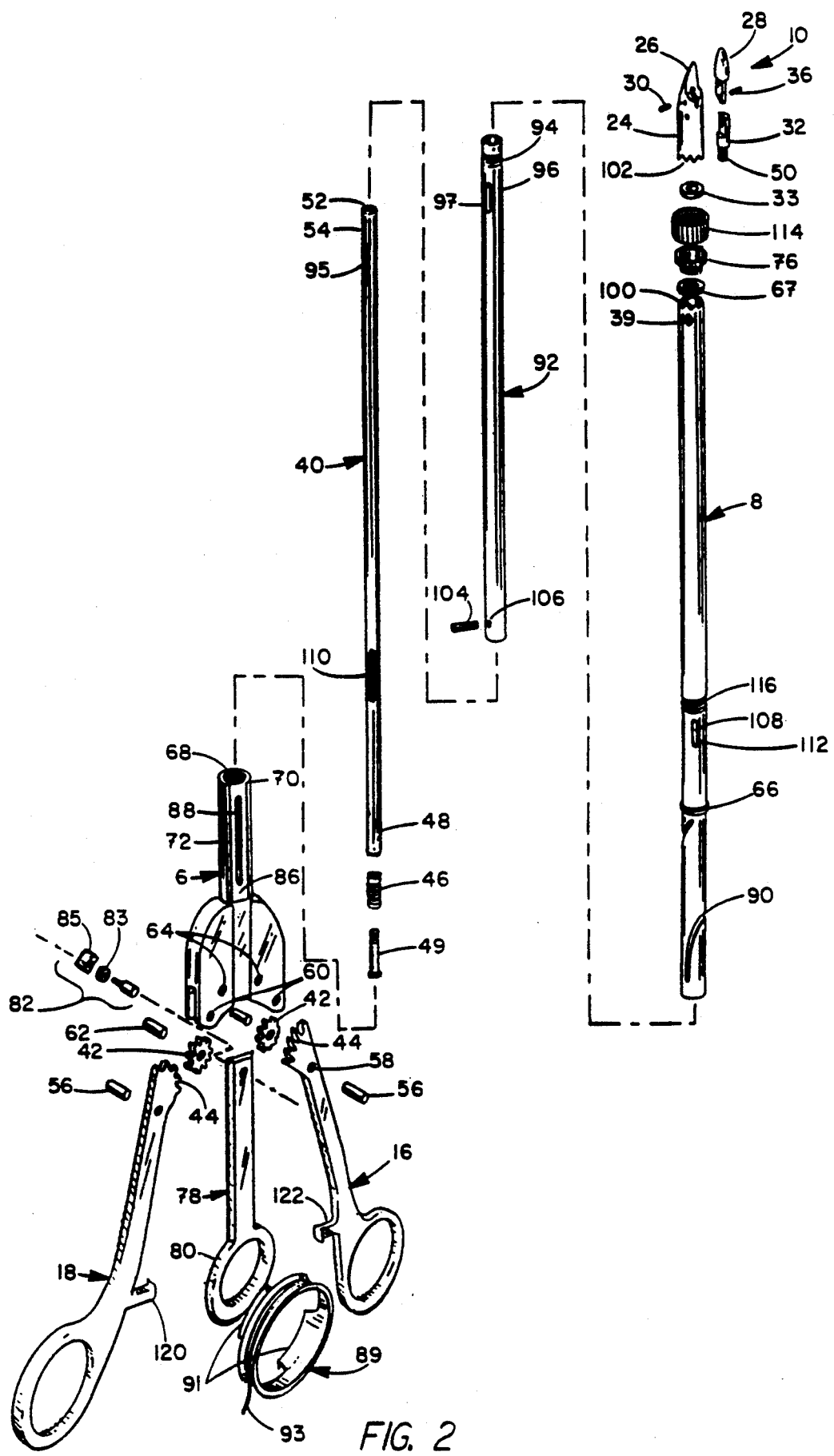
FIG. 2 is an exploded isometric view of the needle manipulator of FIG. 1.
Figure 3D:
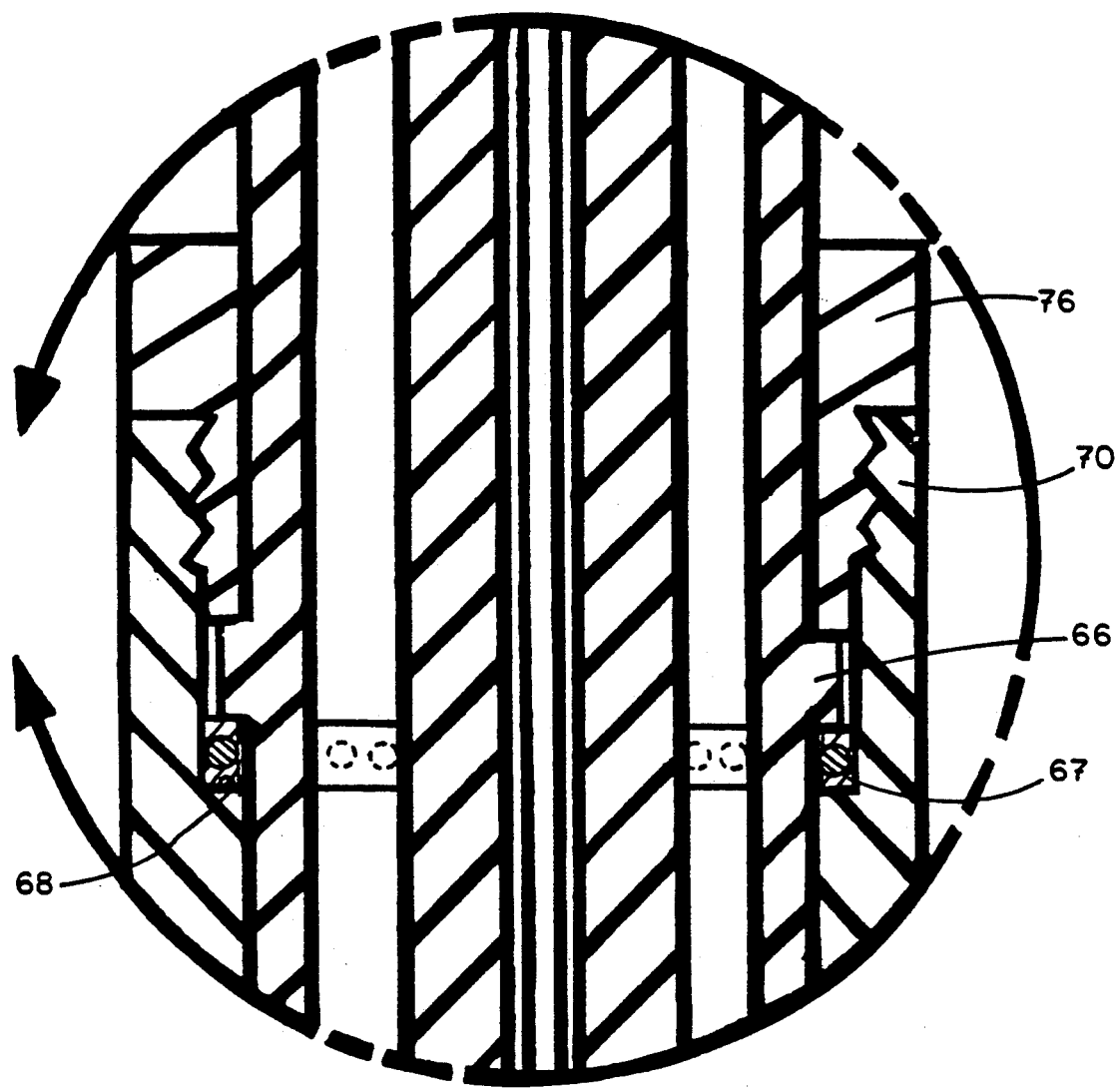
Figure 4:
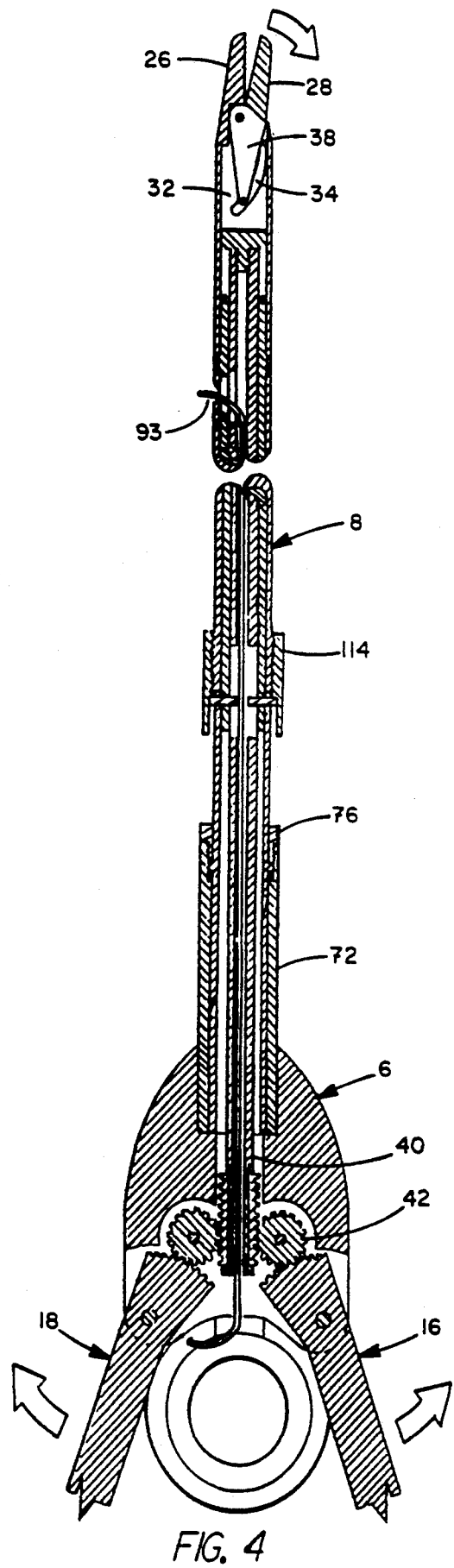
FIG. 4 shows the needle manipulator of FIG. 3 with the jaws in the open position.
Figure 5:
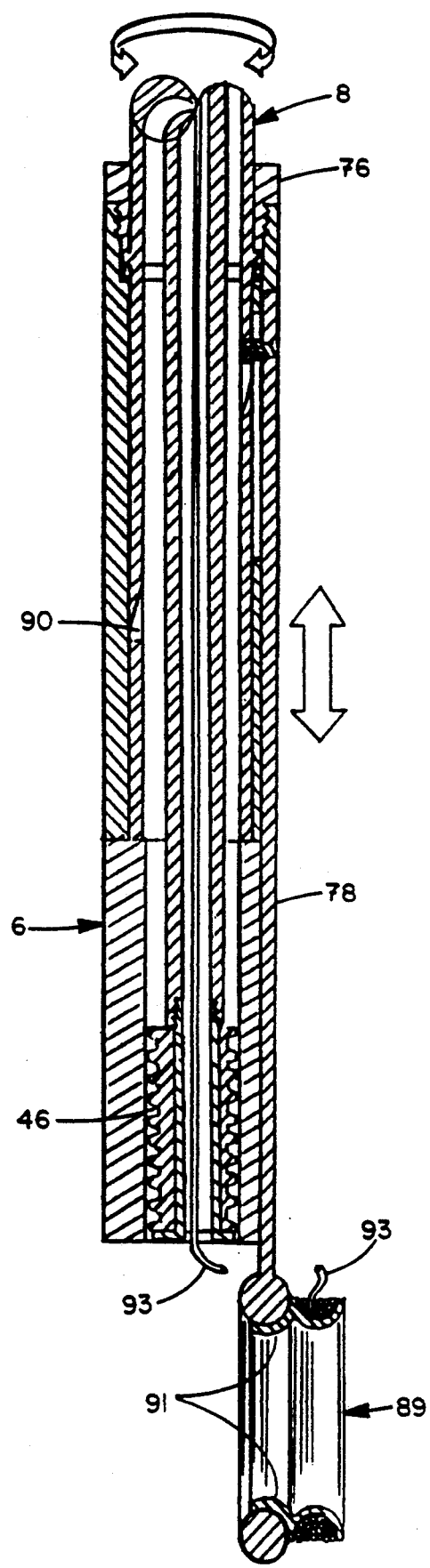
FIG. 5 is a cross-sectional view of a portion of the needle manipulator of FIG. 1 taken in a plane perpendicular to the plane of FIG. 3.
Figure 7:
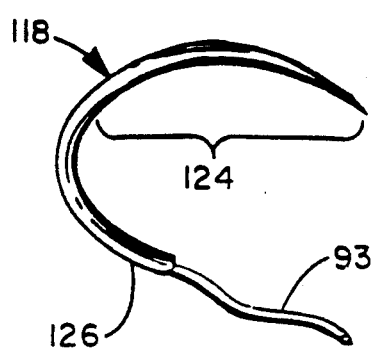
FIGS. 7 and 7A are enlarged plan and side views of the needle of FIG. 6 showing the attachment of the suture material and the special shape of the needle.
Figure 7A:
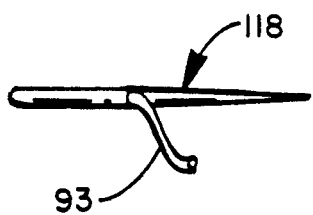
Figure 7B:
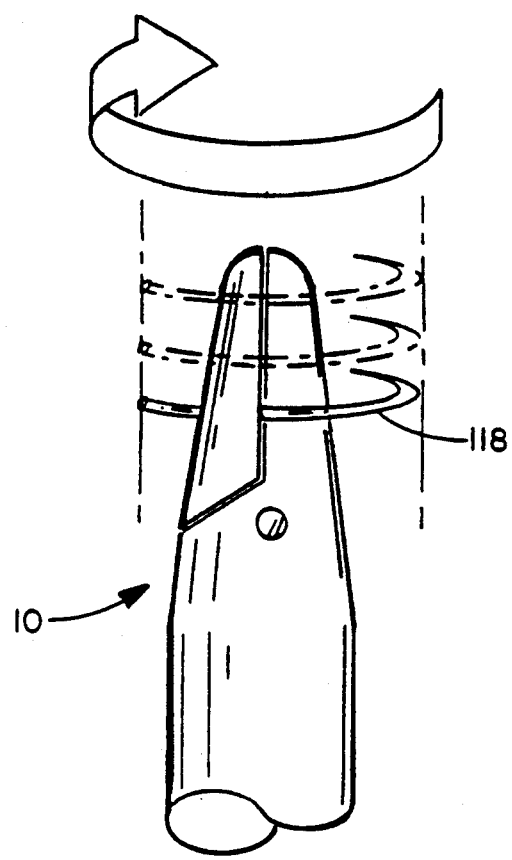
FIG. 7B illustrates the progression of the needle of FIG. 6 after successive stitches caused by rotation of the tip assembly and needle.
Figure 8A:
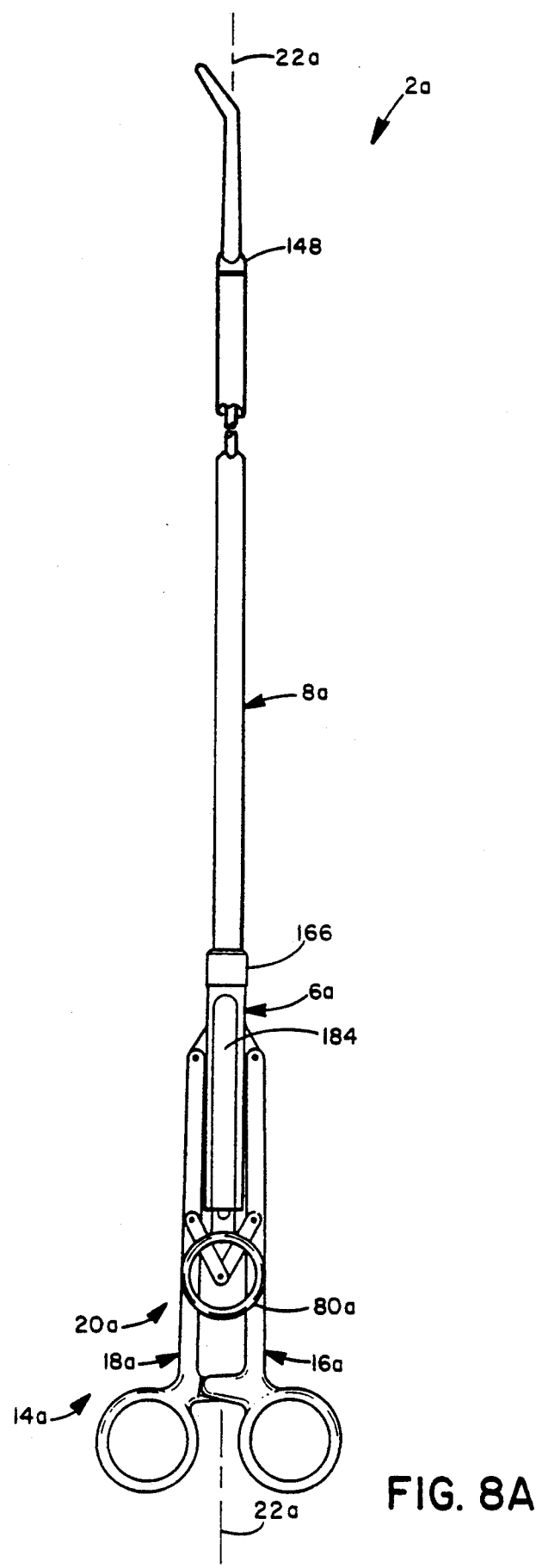
FIGS. 8A, 8B and 8C are side views of a grasping type of endoscopic medical instrument made according to the invention shown in a closed jaw position in FIG. 8A, an open-jaw position in FIG. 8B with the tip assembly rotated 90° from the position of FIG. 8A, and a closed jaw position in FIG. 8C with the tip assembly rotated 180° from the position of FIG. 8A.
Figure 8B:
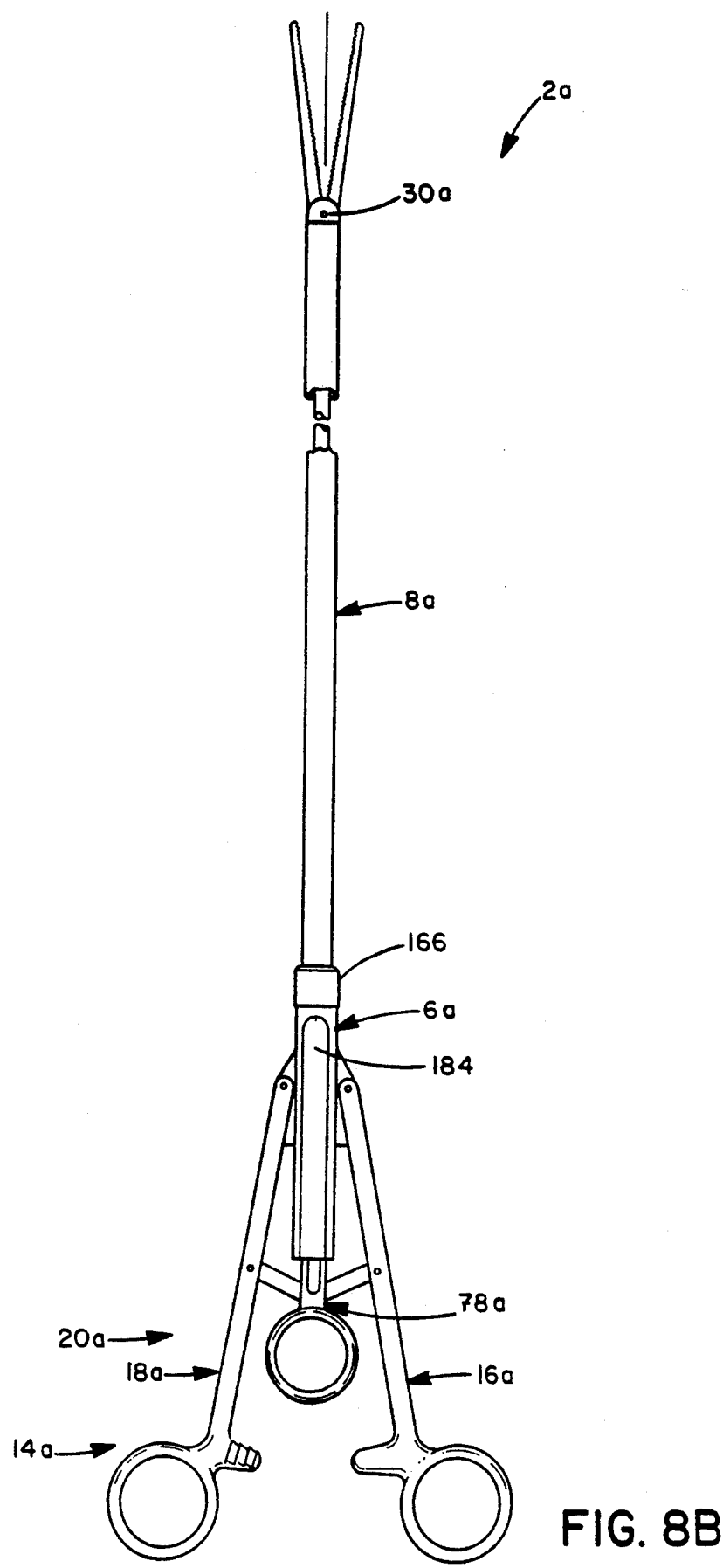
Figure 8C:
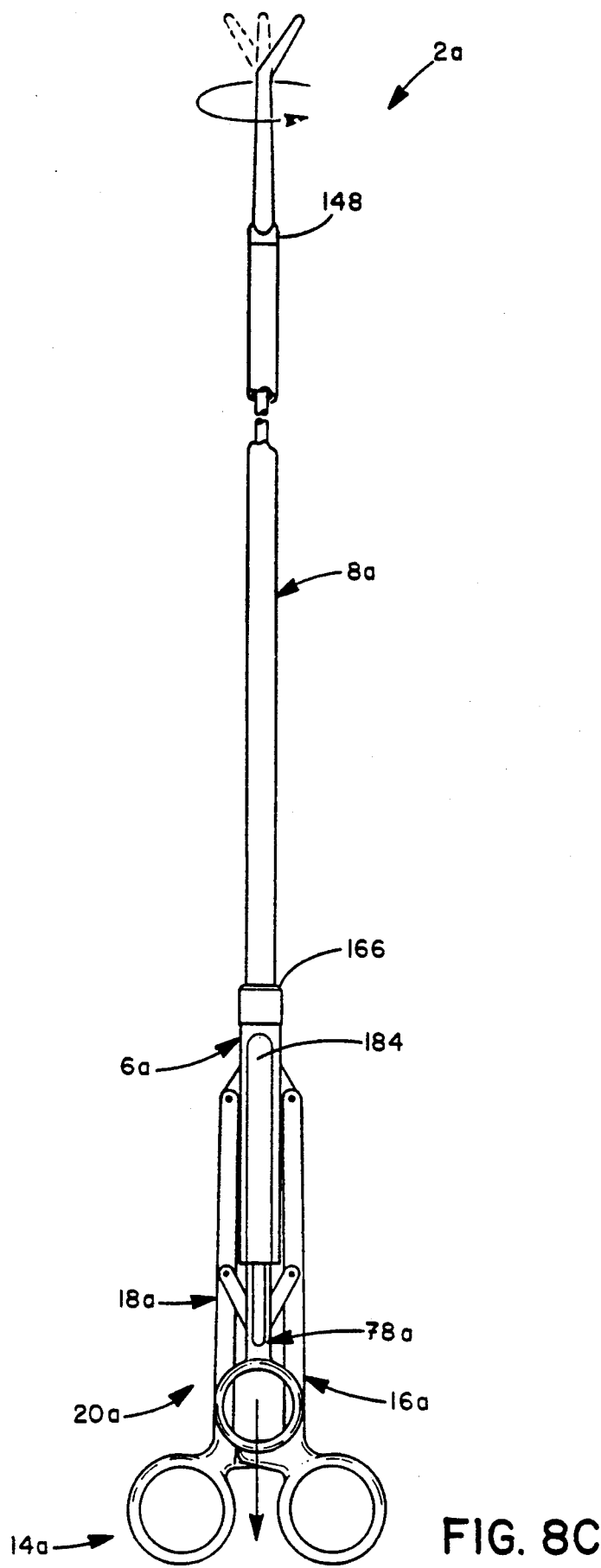

FIG. 2 illustrates tip assembly 10 as including a tip 24 having a fixed jaw 26 integral with tip 24 and a movable jaw 28 secured to tip 24 by a pivot pin 30. Tip assembly 10 also includes an adapter 32 sized to fit within and slide within the hollow interior of tip assembly 10. Adapter is held within the interior of tip 24 by a ring 33 press fit into the tip interior. Adapter 32 has a cam slot 34 within which a drive pin 36 extending from an end 38 of movable jaw 28 rides. Thus, axial movement, that is movement parallel to axis 22, of adapter 32 causes movable jaw 28 to move from the closed jaw position of FIG. 3 to the open jaw position of FIG. 4. This is accomplished by the manipulation of jaw driver assembly 14. (See FIG. 1.)

Jaw driver assembly 14 includes finger and thumb loops 16, 18 coupled to an axial drive rod 40 through the engagement of idler gears 42 with drive gear segments 44 formed on finger and thumb loops 16, 18 and a rotary rack 46 formed on the proximal end of 48 of drive rod 40. Rack 46 is secured to end 48 by a screw 49 to permit rack 46 to rotate freely. Adapter 32 includes a threaded tip 50 which engages a threaded hole 52 at the distal end of 54 of rod 40. Finger and thumb loops 16, 18 are pivotally mounted to base 6 through the use of pivot pins 56 passing through pivot holes 58 formed in loops 16, 18 and pivot pin bores 60 formed in base 6. Idler gears 42 are secured to base 6 by idler gear pins 62 which pass through bores in the idler gears and through idler gear pin holes 64 in base 6.

Tip carrier tube 8 has an annular shoulder 66 sized and positioned to seat against a thrust bearing 67 supported by an internal annular surface 68 formed at the distal end 70 of barrel portion 72 of base 6. See FIG. 3D. The proximal end 74 of tube 8 is maintained within base 6 by an externally threaded ring 76. Ring 76 is sized so that when the ring is secured against distal end 70 of barrel portion 72, tube 8 is securely mounted to base 6 but is free to rotate within the base. Thrust bearing 67 helps to ensure the free rotation of tube 8 during use.

Jaw rotator assembly 20 includes a rotary actuator trigger 78 having a finger loop 80 at its proximal end and a cam pin 82 at its distal end. Trigger 78 incudes elongate portion 84 having a dovetail or trapezoidal cross-sectional shape which slides within a similarly configured dovetail slot 86 formed along the length of base 6. Pin 82 passes through an axial slot 88 formed in barrel portion 72 along slot 86. Pin 82 passes through slot 88 to engage a spiral groove 90 formed in proximal end 74 of tube 8. Pin 82 includes a ring 83 which rides within slot 88 and a guide 85 which rides within spiral groove 90, both ring 83 and guide 85 preferably made of PTFE. Thus, axial movement of trigger 78 causes pin 82 to ride along spiral groove 90, thus rotating tube 8 and tip assembly 10 therewith about axis 22.

Tip assembly 10 is secured to tip carrier tube 8 using a hollow tip mounting tube 92. Tip mounting tube 92 has external threads 94 at its distal end 96 which engage internal threads 98 formed within the interior of tip 24. Tip 24 and tip carrier tube 8 have opposed, complementary tooth surfaces 100, 102 which, when engaged, keep tip assembly 10 from rotating relative to tip carrier tube 8. Tube 8, mounting tube 92 and drive rod 40 are secured to one another by a common pin 104. Pin 104 passes through a bore 106 in mounting tube 92, a short slot 108 in carrier tube 8 and a long slot 110 in drive rod 40. Common pin 104 is maintained at the proximal end 112 of slot 108, thus keeping tooth surfaces 102, 100 engaged, through the use of an internally threaded ring 114 threaded onto external threads 116 formed on the outside of tube 8 adjacent slot 108. Slot 110, being longer than slot 108, can still move axially through the manipulation of finger and thumb loops 16, 18, thus causing jaws 26, 28 to open and close.

A suture material supply spool 89 is mounted to finger loop 80 through the use of snap flanges 91 which engage the inside of the finger loop. Suture material 93 is directed from needle 118, through hole 99 in tube 8, through slots 95, 97 in rod 40 and tube 92, through the center of rod 40 and is wound about spool 89.

The operation of needle manipulator 2 will now be described. The user places his or her thumb and middle finger through thumb and finger loops 18, 16. Loops 18, 16 are separated, as suggested in FIG. 4, causing drive gear segments 44 to rotate idler gears 42 which, in turn, drive rotary rack 46 axially, that is parallel to axis 22. This causes adapter 32 to move axially so that drive pin 36 moves along cam slot 34, thus opening jaws 26, 28 through the pivotal movement of movable jaw 28. A needle 118 is placed between jaws 26, 28 and is secured in place by moving finger loops 16, 18 back towards one another to the position of FIGS. 1 and 3. Needle 118 is locked between jaws 26, 28 through the engagement of catches 120, 122 carried by loops 16, 18. The manipulation of rotary actuator trigger 78 parallel to axis 22 causes pin 82 to ride along spiral groove 90, thus rotating tip carrier tube 8 and tip assembly 10 therewith about axis 22. Tip mounting tube 92 and axial drive rod 40 are likewise rotated about axis 22 upon the actuation of trigger 78 due to the interlocking engagement of common pin 104 with all three members. With needle manipulator 2, the user's hand, wrist and arm can be generally aligned with axis 22 for enhanced control.

The reciprocal movement of trigger 78 causes tip assembly 10 and needle 93 to move in opposite rotary directions. See FIGS. 6, 6A and 6B. In the preferred embodiment this movement is through an arc of about 240°. Only when needle 93 is moved in the appropriate rotary direction, clockwise in FIG. 6, will the needle pierce tissue 128. After the piercing movement, the user releases needle 118 from between jaws 26, 28, rotates tip assembly 10 in the opposite direction, regrasps needle 118 between jaws 26, 28, pulls needle 118 completely through tissue 128, repositions needle 118 between jaws 26, 28 at a position 126 along the needle and repeats the process.

Needle 118 has a generally elliptical shape with a main portion 124 having a generally circular shape. Needle 118 can be grasped between jaws 26, 28 at a position 126 adjacent the attachment point for suture material. Point 126 is located at about the center of the generally circular arc formed by a main portion 124 so that when tip assembly 10 is rotated about axis 22, main portion 124 moves along a generally circular path. This minimizes trauma to tissue 128 and makes the procedure easier to perform.

Turning now to FIGS. 8-10B, an alternative embodiment of the endoscopic medical instrument of FIGS. 1-7B is shown. Parts of the alternative embodiment which correspond to the embodiment of FIG. 1 have like reference numerals. The alternative embodiment is an endoscopic medical instrument of the grasping type having a pair of movable jaws 28a, 28b as part of the tip assembly 10a Instrument 2a includes broadly an elongate body 4a, a tip assembly 10a removably mounted to the distal end 12a of a tip carrier tube 8a, a driver assembly 14a, which causes jaws 28a, 28b to move between their open and closed positions, and a jaw rotator assembly 20a, which causes tip assembly 10a, and jaws 28a, 28b therewith, to rotate about axis 22a.

Jaws 28a, 28b include outer portions 140 and arm portions 142 connected by hubs 144 having holes 146 formed therein. Tip assembly 10a also includes a circular, hollow tip coupler plug 148 having a through hole 150 formed perpendicular to axis 22a. Jaws 28a, 28b are mounted within tip coupler plug 148 and are pivotally secured within the plug by pivot pin 30a. The interior of tip coupler plug 148 is sized to permit jaws 28a, 28b to move between their open and closed positions of FIGS. 8A and 8B.

Figure 10A:
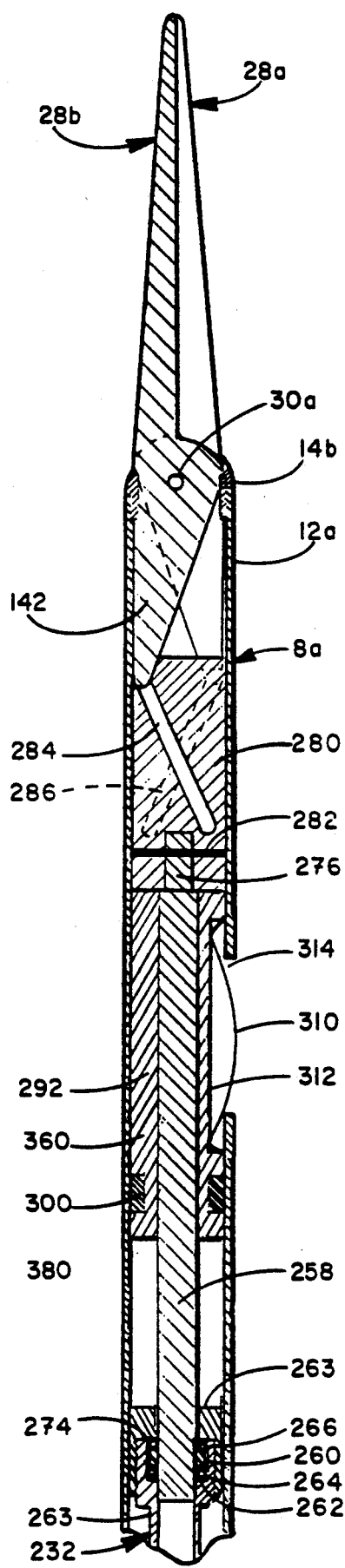
FIGS. 10A and 10B are longitudinal cross-sectional views of the distal and proximal portions of the instrument of FIGS. 9A and 9B.
Figure 10B:
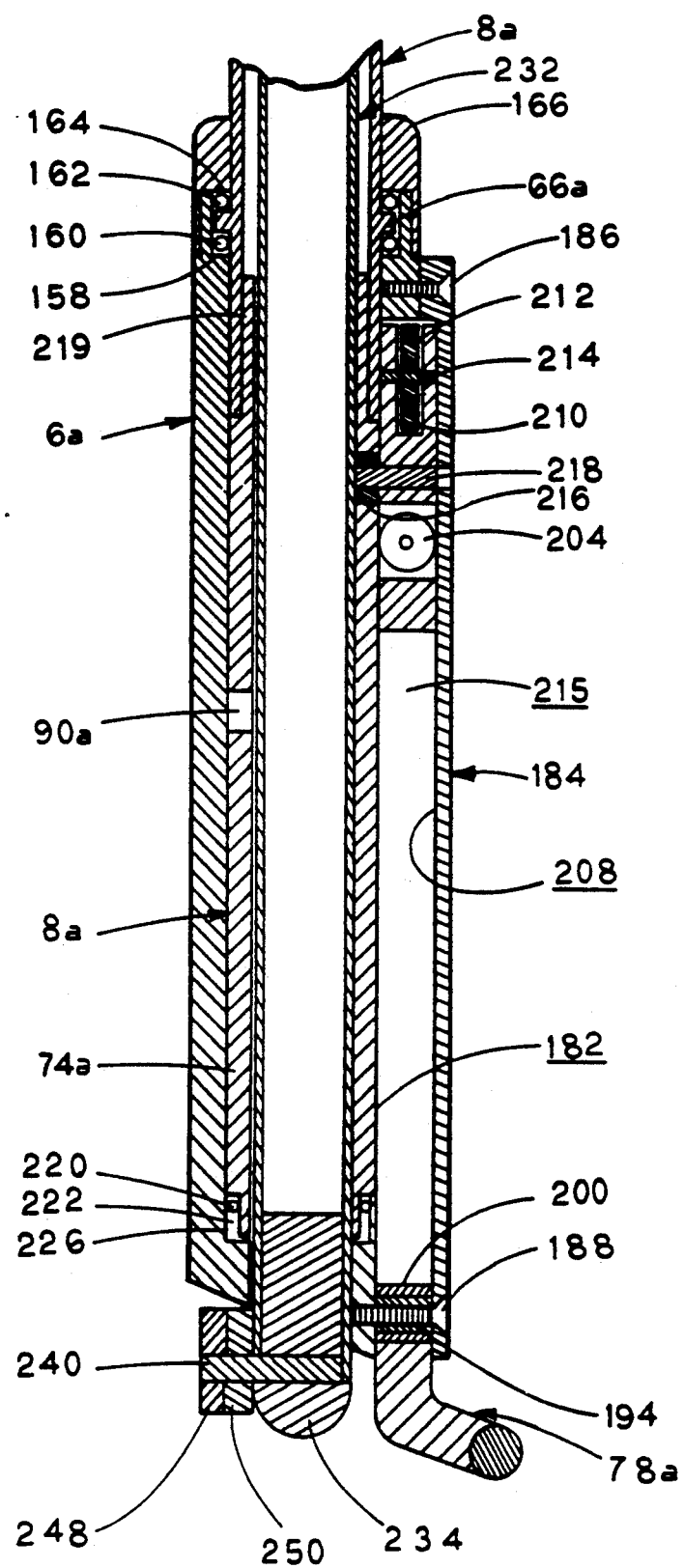

Tip coupler plug 148 has external threads 152 formed on one end. Threads 152 are sized to engage internal threads 154 formed at distal end 12a of tip carrier tube 8a. In this way, tip assembly 10a can be removably secured to body 4a of instrument 2a. Tip carrier tube 8a is sized so that proximal end 74a fits within the hollow interior 156 of base 6a. Base 6a, as shown in FIG. 10B, has an inner shoulder 158 which supports annular shoulder 66a of tip carrier tube 8a. A set of ball bearings 160 is positioned between shoulder 66a and shoulder 158. Another set of ball bearings 162 is situated between annular shoulder 66a and an inner shoulder 164 of a tip carrier tube retaining nut 166. Nut 166 has a threaded interior 168 which engages the threaded exterior 170 of base 6a. Shoulders 158, 164 are positioned so that tip carrier tube 8a is secured axially to base 6a but is allowed relatively free rotary movement with respect to the base by virtue of ball bearing sets 160, 162.

Finger and thumb loops 16a, 18a are pivotally mounted to lugs 172 of base 6a using pins 174 which pass through openings 176 formed in the clevis ends 178 of loops 16a, 18a and corresponding holes 180 formed in lugs 172. Manipulation of loops 16a, 18a is used to open and close jaws 28a, 28b and will be discussed below.

Base 8a has flat face 182 extending substantially along its entire length. A hollowed out cover 184 is secured to base 6a by a pair of screws 186, 188. Screw 186 threads into a hole 190 in base 6a adjacent the distal end of flat face 182. Screw 188 passes through the hollow interior 192 of a standoff 194 and engages a threaded hole 196 formed in flat face 182 at the proximal end of axial slot 88a. A roller 200 is sized to be mounted over and rotate freely about standoff 194. Roller 200 is sized to fit within a slot 202 formed in trigger 78a and helps to stabilize trigger 78a as the trigger moves parallel to axis 22a. The stability of trigger 78a is also aided by the use of a pair of rollers 204 on either side of trigger 78a at the distal end 206 of the trigger. Rollers 204 ride between surface 182 and the overlying surface 208, as seen in FIG. 10B, of cover 184. Side to side movement of distal end 206 of trigger 78a is restricted by engagement of a roller 210 mounted in a slot 212 at distal end 206 of trigger 78a by a pin 214. Roller 210 is sized to ride along the side surfaces 215 of the hollow interior of cover 184.

Trigger 78a also includes a cam pin 82a. Cam pin 82a includes a cam roller 216 secured to distal end 206 by a pin 218. Cam pin 82a is positioned to extend through axial slot 88a and engage spiral groove 90a at proximal end 74a of tip carrier tube 8a. Thus, axial movement of trigger 78a causes cam pin 82a to move along spiral groove 90a, thus rotating tip carrier tube 8a and tip assembly 10a therewith about axis 22a.

FIG. 10B shows that proximal end 74a is thicker than the remainder of base 8a. This is to provide a deeper spiral groove 90a and thus a better camming surface for cam roller 216 to ride against. This dual wall thickness is achieved by overlapping tubes having different wall thicknesses as shown at overlapping region 219.

Lateral support of proximal end 74a within base 6a is aided by the use of a set of ball bearings 220 housed within an annular cavity 222. Cavity 222 is defined between the tip 224 of end 74a and a cupped shaped region 226 formed within base 6a adjacent proximal end 198.

Figure 9A:
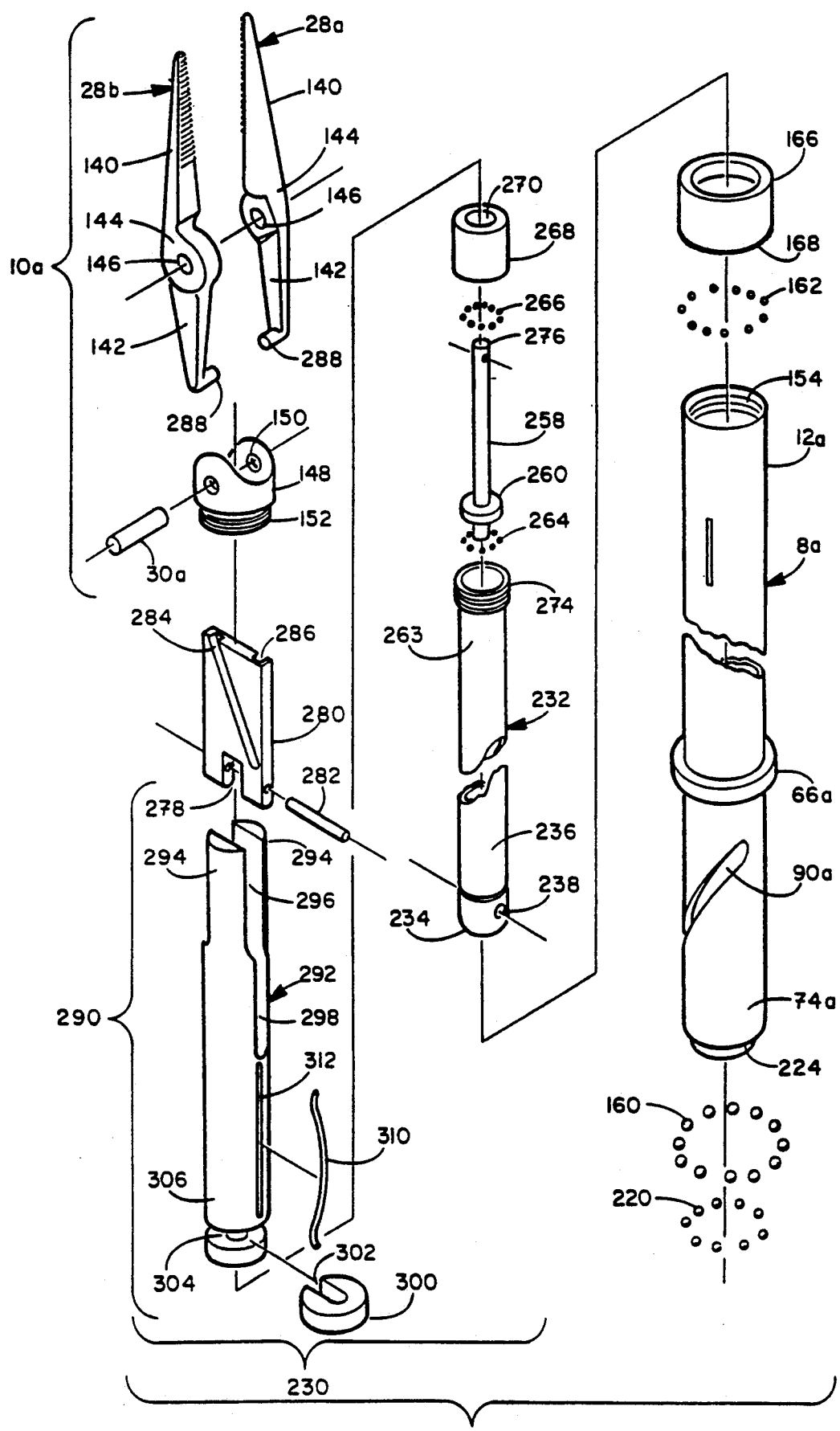
FIGS. 9A and 9B are exploded isometric views of the distal and proximal portions of the instrument of FIG. 8 shown with straight rather than doglegged jaws.

The remainder of jaw driver assembly 14a, in addition to finger and thumb loops 16a, 18a, will now be discussed. As shown in FIG. 9A, an axial drive tube assembly 230 includes an axial drive tube 232 having a plug 234 at a proximal end 236. Plug 234 has a transverse bore 238 through which a common pin 240 passes. Pin 240 also passes through aligned bores 242 formed in the overlapping ends 244, 246 of links 248, 250. Links 248, 250 are pivotally connected to finger and thumb loops 16a, 18a by pins 252 passing through holes 254, 256 formed in links 248, 250 and loops 16a, 18a. Thus, movement of finger and thumb loops 16a, 18a towards and away from each other causes links 248, 250 to articulate, thus driving axial drive tube 232 along axis 22a.

Axial drive tube assembly 230 also includes a flanged draw bar 258 with a flange 260 at a proximal end thereof. Flange 260 is sized to lie adjacent an internal shoulder 262 formed at the distal end 263 of tube 232 with a set of ball bearings 264 captured therebetween. A second set of ball bearings 266 is positioned on the other side of flange 260. A draw bar retaining nut 268 has a central bore 270 sized to fit over flanged draw bar 258. Nut 268 has an internal shoulder 272 which rests against the lip 274 of tube 232 to capture ball bearings 266 between nut 268, bar 258 and tube 232. Flanged draw bar 258 is thus fixed axially to axial drive tube 232 but is allowed to freely rotate within the axial drive tube.

The distal end 276 of bar 258 fits within a cut-out region 278 formed in a flattened rectangular cam block 280. Cam block 280 is secured to distal end 276 by a pin 282 passing through both. Cam block 280 has a pair of slots 284, 286 formed on either side of cam block 280 and angled in opposite directions. Arms 142 of jaws 28a, 28b each have inwardly extending pins 288 sized to engage slots 284, 286. Thus, axial movement of axial drive tube 232, which also moves flanged draw bar 258 and cam block 280 therewith, causes cam block 280 to move parallel to axis 22a thus causing pins 288 to slide along slots 284, 286; this causes jaws 28a, 28b to open and close in a grasping action.

Axial drive tube assembly 230 also includes a fork assembly 290 for stabilizing cam block 280 during use. Fork assembly 290 includes a fork 292 having a pair of arms 294 defining wider and narrower gaps 296, 298 therebetween. Wider gap 296 is sized to encompass arms 142 of movable jaws 28a, 28b while narrower gap 298 is sized to lie along either side and guide cam block 280.

Fork assembly 290 also includes a U-collar 300 having a slot 302 formed therein. Slot 302 is sized to fit loosely within an annular groove 304 formed at the proximal end 306 of fork 292. The outer circumference of U-collar 300 is sized to create a relatively tight friction fit within the interior 308 of tip carrier tube 8a. Thus, fork assembly 290 is fixed axially within tip carrier tube 8a while flanged draw bar 258 moves axially with fork 292.

Fork assembly 290 also includes a spring 310 partially housed within a fork spring slot 312 formed in fork 292 between groove 304 and narrower gap 298. Spring 310 is sized and positioned to engage a tube spring slot 314 formed in tip carrier tube 8a. In this way, fork assembly 290 is kept from rotating axially within tip carrier tube 8a. However, when first mounting tip assembly 10a to distal end 12a of tip carrier tube 8a, the user can depress spring 310 and allow fork assembly 290 to rotate along with cam block 280, tip assembly 10a and flange draw bar 258 until tip coupler plug 148 is screwed fully onto threads 154 of tip carrier tube 8a. At this point, spring 310 is allowed to freely enter slot 314 to prevent fork assembly 292 from rotating within tip carrier tube 8a. Thus, fork assembly 290 is used for two primary purposes: to guide and stabilize cam block 280 and arms 242 of jaws 28a, 28b and to keep tip assembly 10a from unscrewing from tip carrier tube 8a.

In use, assuming tip assembly 10a must be changed, spring 310 is depressed through slot 314 and tip assembly 10a is unscrewed from internal threads 154 at distal end 12a of tip carrier tube 8a. An appropriate tip assembly is then threaded onto distal end 12a. Using tip assembly 10a, pins 288 are guided into slots 284, 286 to permit both jaws 28a, 28b to move. In appropriate cases, a different cam block 280 could be used to accommodate a different type of motion; also, the tip assembly could be constructed so that only one jaw moves. Tip assembly 10a is rotated about axis 22a by the manipulation of trigger 78a. The axial movement of trigger 78a causes tip carrier tube 8a and tip assembly 10a secured thereto to rotate about axis 22a. Once properly oriented, the user opens and shuts jaws 28a, 28b by opening and closing finger and thumb loops 16a, 18a. Doing so articulates links 248, 250 which are coupled to axial drive tube 232 through common pin 240 and plug 234. Axial movement of drive tube 232 causes like axial movement of drawbar 258 which, being pinned to cam block 280 by pin 282, moves the cam block axially along axis 22a. The axial movement of cam block 280 causes transverse pivotal movement of jaws 28a, 28b as pins 288 ride along slots 284, 286 to provide the desired grasping action.

The invention has been shown in two different embodiments, one specially adapted as an endoscopic needle manipulator while the other as an endoscopic tissue grasper or manipulator. The invention can also be practiced using tips and tip assemblies configured for other uses. For example, tip assemblies adapted for dilating a region, cutting tissue, stapling tissue or knotting suture material could be used as well.

Figure 11:
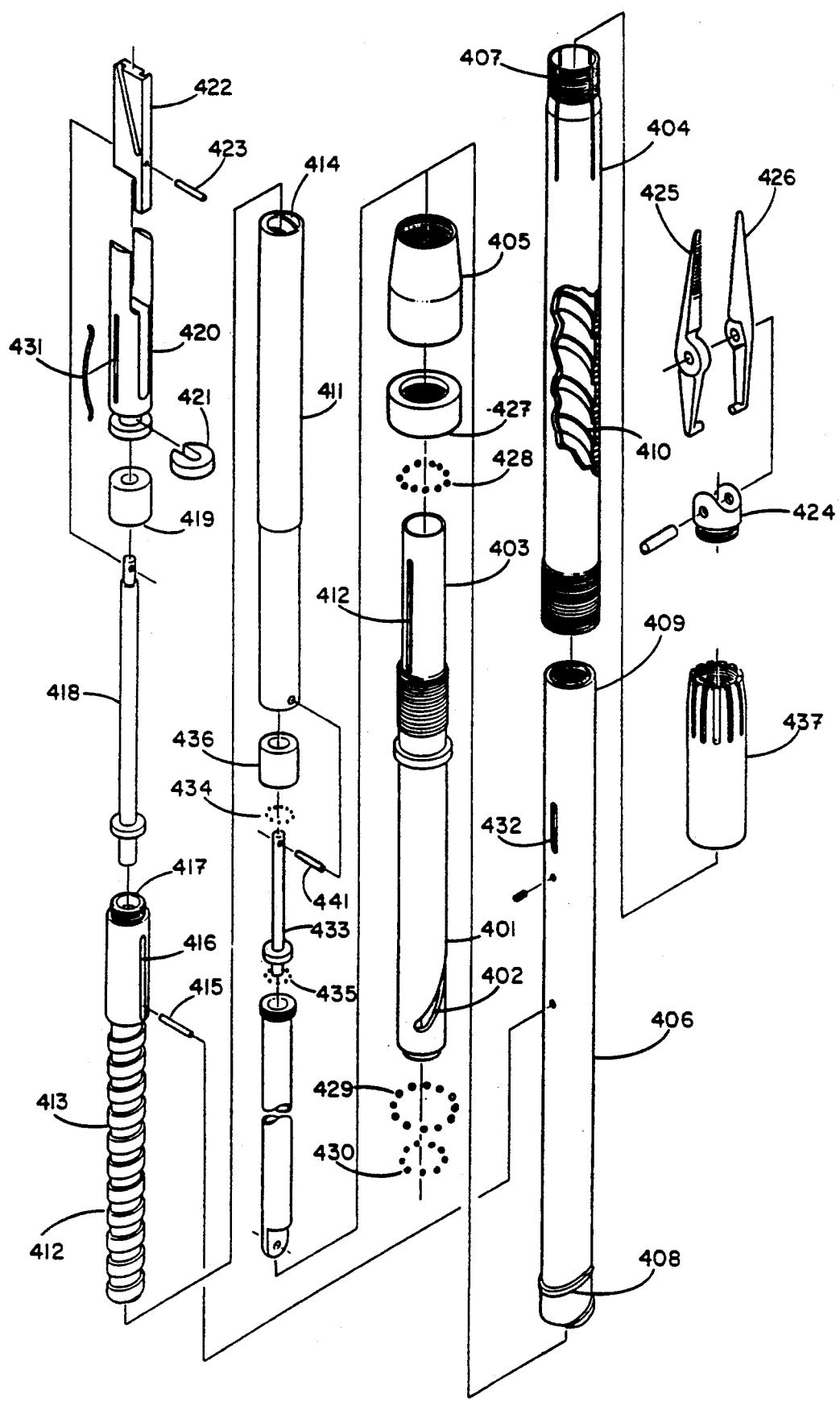
FIG. 11 is an exploded view of an embodiment of the invention which shows the axial extension capability of the instrument.

Turning now to FIG. 11, an embodiment of the invention is shown which permits the user to extend the length of the instrument and thereby advance the tip assembly without advancing the proximal end of the instrument. A tube 401 with a spiral groove 402 at the proximal end thereof serves the same function as the corresponding spiral groove 90 on he proximal end 74 of the tube 8 in the embodiment of FIG. 2. Fitting over the distal end 403 of the tube 401 in this embodiment however is a barrel 404, which is secured to the tube 401 by an adaptor nut 405. Passing through the barrel 404 is a hollow spindle 406 which exceeds the barrel in length and protrudes from the distal end 407 of the barrel. The spindle 406 contains a broad thread 408 formed on its exterior surface beginning at the proximal end and extending only a short distance along the spindle. This broad thread is mated with a corresponding thread 410 along the inner surface of the barrel 404, extending substantially the full length of the barrel. A typical pitch of the thread is five threads to the inch. The distal end 409 of the spindle 406 which protrudes from the distal end 407 of the barrel 404 may thus be turned by one's fingers, which will cause the thread 408 on the external surface of the spindle to travel along the thread along the internal surface of the barrel, and thereby cause the spindle to move axially within the barrel.

This axial movement of the spindle 406 relative to the barrel 404 is matched by a corresponding axial movement of smaller diameter elements retained inside the spindle and barrel, which in turn communicate the axial movement to the tip assembly. These inner, smaller diameter elements include a hollow draw tube 411 and a draw bar 412 which passes through the draw tube 411. The draw bar 412 has broad threads 413 formed along its outer surface, and these are mated to corresponding broad threads 414 along the inner surface of the draw tube 411. These threads are of the same pitch as the threads 408 on the spindle 406.

A pin 415 affixed to the spindle 406 and extending inward engages a slot 416 on the draw bar, and thus the turning of the spindle causes a simultaneous turning of the draw bar. Since the threads 413 on the draw bar are of the same pitch as the thread 408 on the spindle, the turning of the spindle causes the draw bar to turn at the same rate and advance relative to the draw tube 411 at the same linear rate in the axial direction as the spindle relative to the barrel 407.

At the distal end 417 of the draw bar is an extension rod 418, secured to the draw bar by a threaded nut 419. The components at the distal end of the extension bar are a fork assembly 420, a U-collar 421, a cam block assembly 422, a pin 423, jaw pivot 424, and a pair of jaws 425, 426, which are analogous to those of the embodiment shown in FIG. 9A, and operate in the same manner. A locking spring 43i extends outward from the fork assembly 420 to extend into a slot 432 in the spindle. This joins the fork assembly to the spindle.

Secured to the proximal end of the draw tube 411 are a second draw bar 433, two ball bearing races 434, 435 and a nut 436, which are analogous to and function in the same manner as the corresponding elements in the embodiment of FIG. 9A. Other elements included in the structure and associated with the tube 401 containing the spiral groove are a retaining nut 427 and three sets of ball bearings 428, 429, 430. Each of these elements is analogous to and serves the same function as the corresponding retaining nut 166 and ball bearings 162, 160, 220 of the embodiment of FIG. 9A.

A further connecting element is a pin 441 which passes through a longitudinal slot 442 in the spiral groove tube 401, as well as the proximal end of the draw tube 411 and the distal end of the second draw bar 433, keeping these three elements in rotational alignment.

The extension of the tip assembly elements is therefore achieved by manually twisting the spindle 406 at a location extending distal to the distal end 407 of the barrel 404. As the spindle and barrel combination are being elongated, the internal draw assembly consisting of the draw bar 412 and draw tube 411 are being elongated at the same rate. This maintains the jaws 425, 426 in harmony with the action of the finger handles, which although not shown in this figure are identical to those shown in FIG. 1. Once the desired extension has been achieved, the spindle 406 may be locked into position relative to the barrel 404 by a clamp nut 437, which compresses the slotted distal end 407 of the barrel down against the spindle. Since the adaptor nut 405 renders the barrel 404 and the spiral groove tube 401 immobile relative to each other, the barrel 404, spindle 406 and spiral groove tube 401 all rotate together once the clamp nut 437 is secured.

Figure 12:
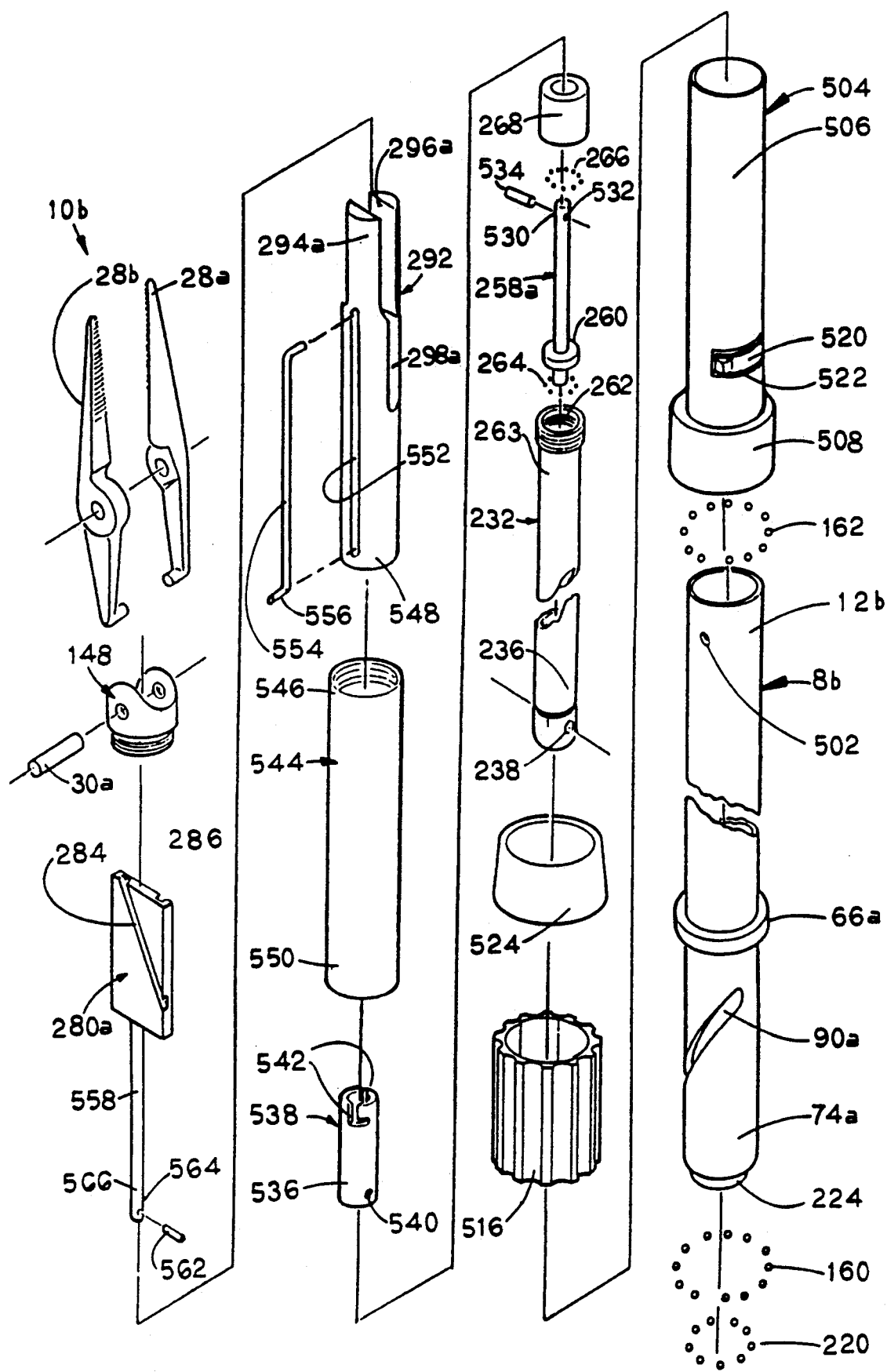
FIG. 12 is an exploded isometric view, similar to FIG. 9A, of the distal portion of an alternative embodiment of the instrument of FIG. 8 in which the user can selectively lock out relative rotary motion between the tube assembly and the body, and also showing a user removable tip assembly.
Figure 13:
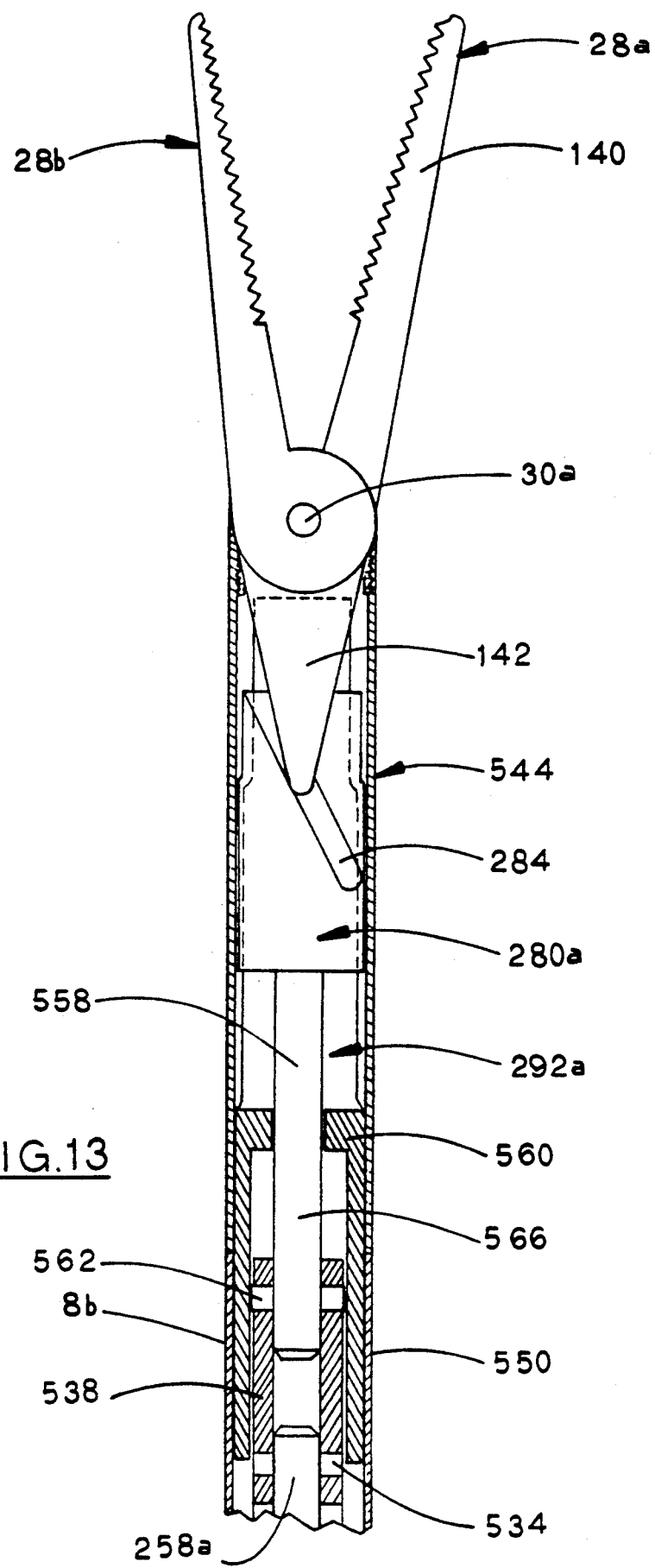
FIG. 13 is an enlarged cross-sectional assembled view of the distal end of the portion of the instrument shown in FIG. 12 with the jaws partially open.
Figure 13A:
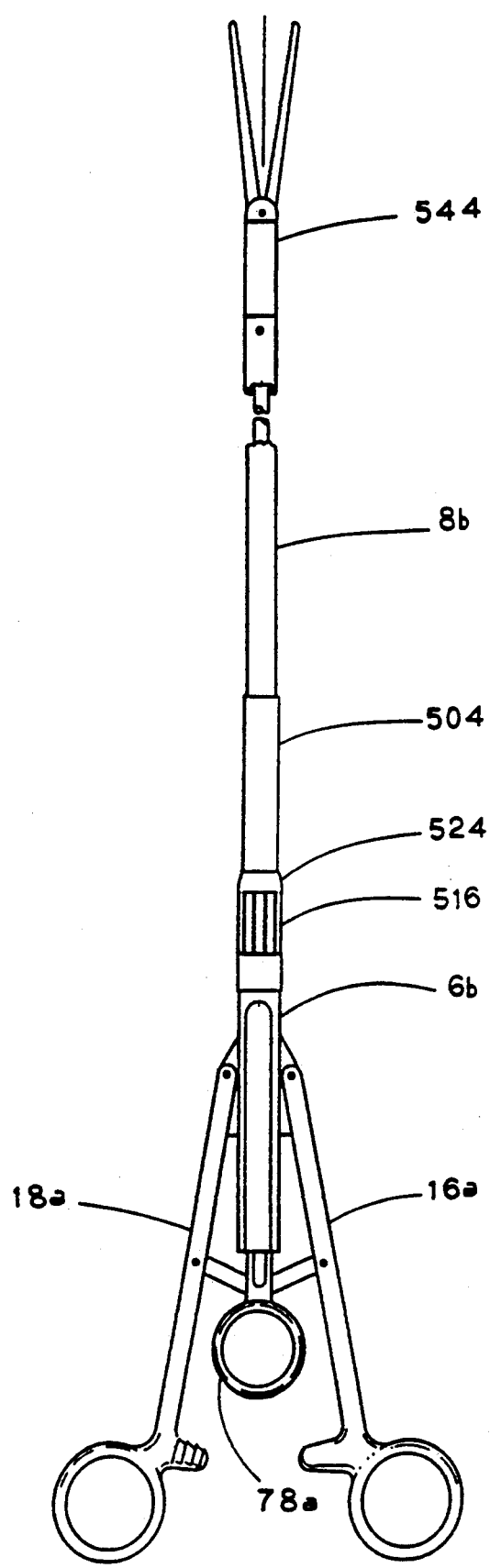
FIGS. 13A and 13B are external views of an alternative embodiment of the instrument of FIG. 8 incorporating the distal portion of FIG. 12 shown in partially open and closed positions.
Figure 13B:
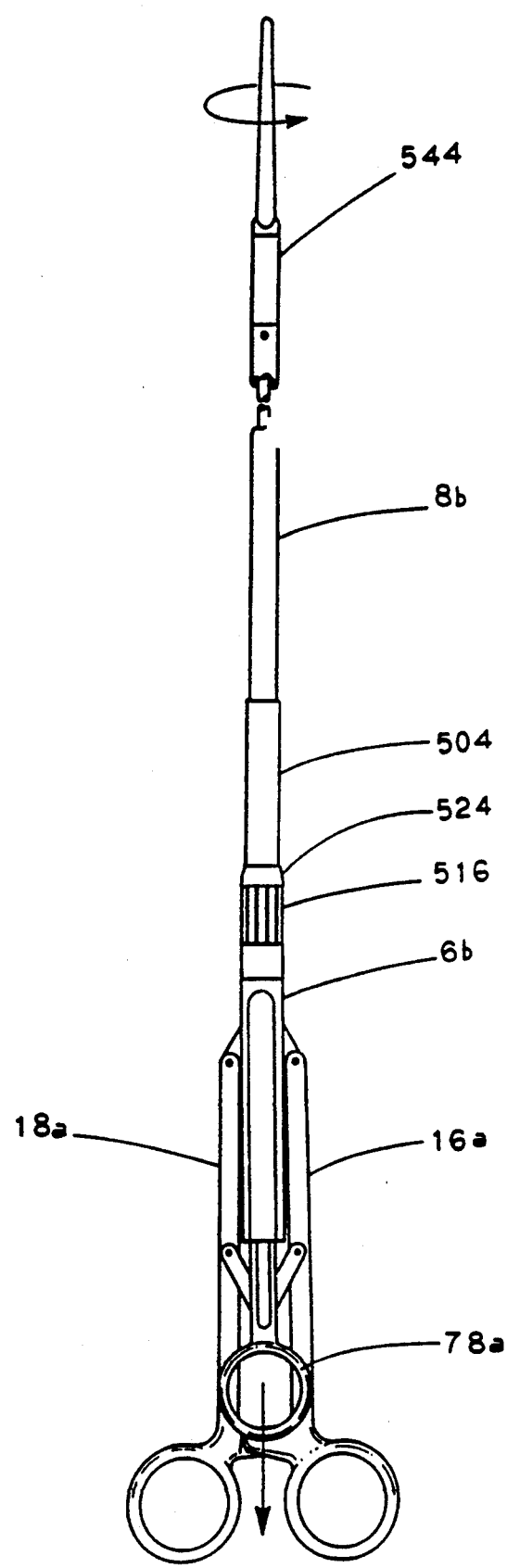
Figure 14:
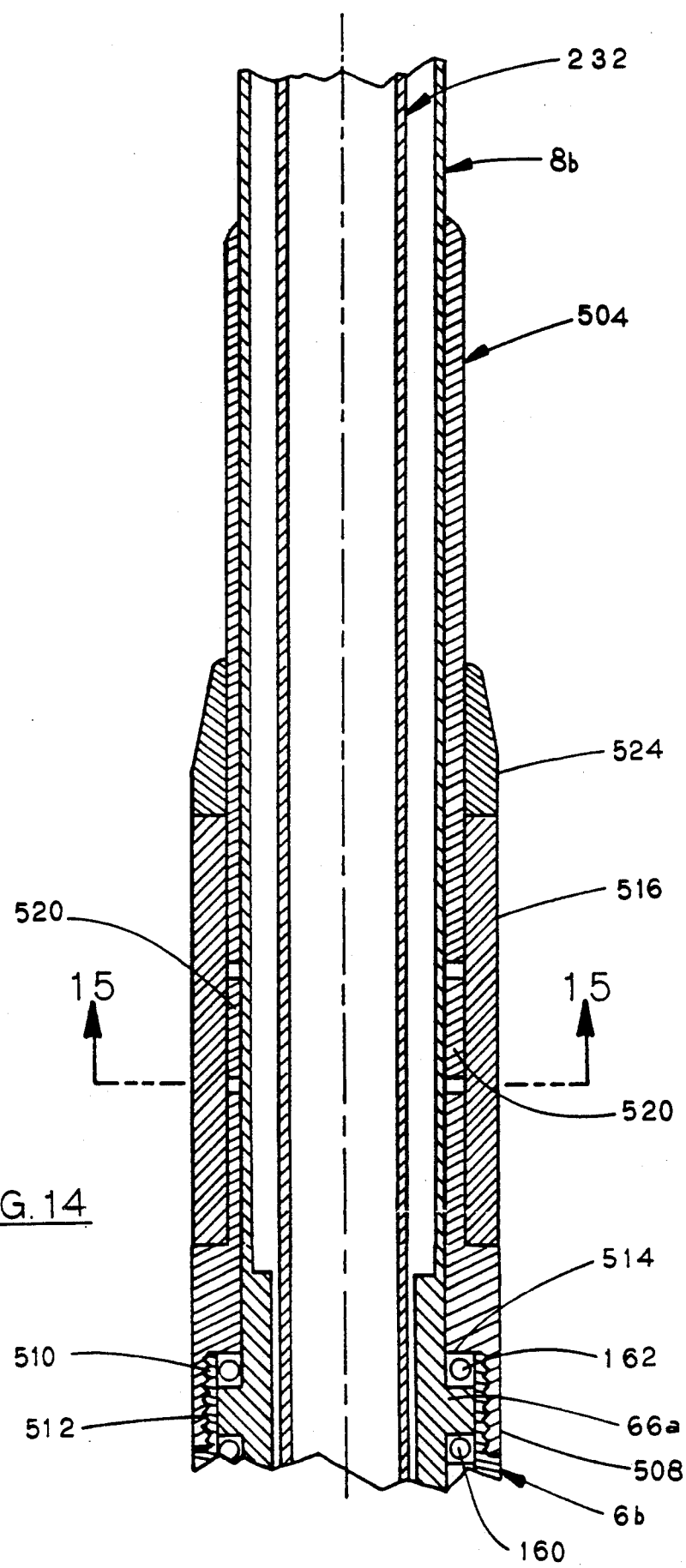
FIG. 14 is an enlarged assembled view of the proximal end of the instrument portion shown in FIG. 12 shown mounted to the base.
Figure 15A:
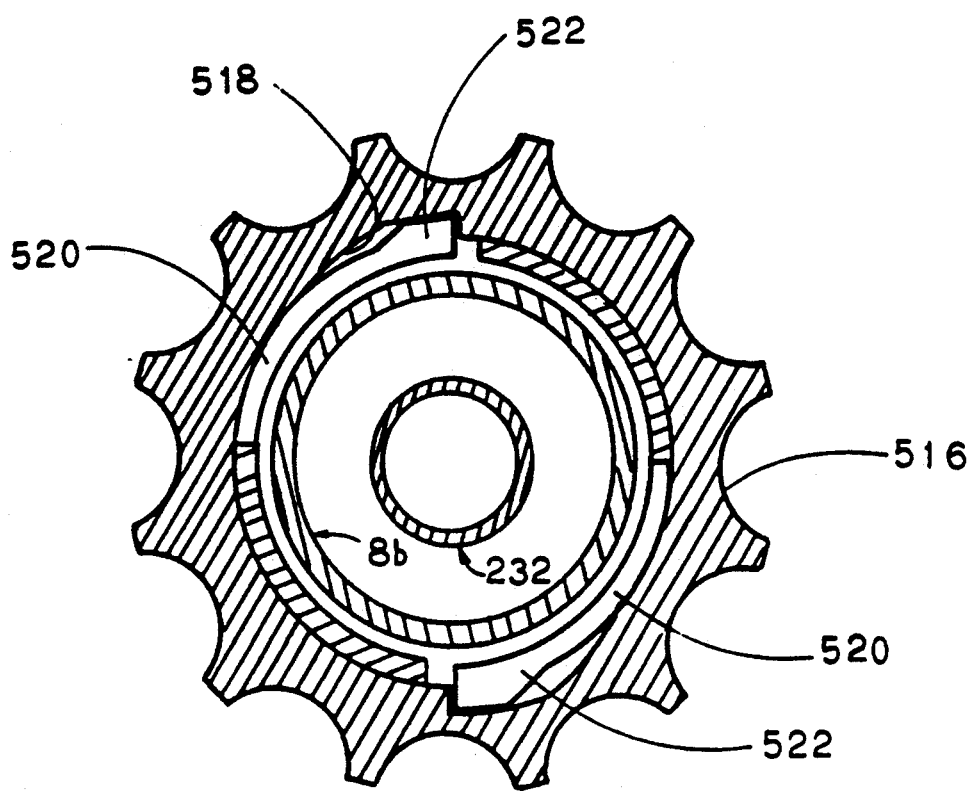
FIGS. 15A and 15B are enlarged cross-sectional views taken along line 15—15 of FIG. 14 showing the serrated lockout collar in its free movement position in FIG. 15A, which allows the tip assembly to rotate freely relative to the body, and the rotary motion lockout position of FIG. 15B, showing the frictional engagement of the lockout fingers, formed as part of the base extension, with the tip carrier tube thereby preventing the tip carrier tube, and the tip assembly therewith, from rotating relative to the base.
Figure 15B:
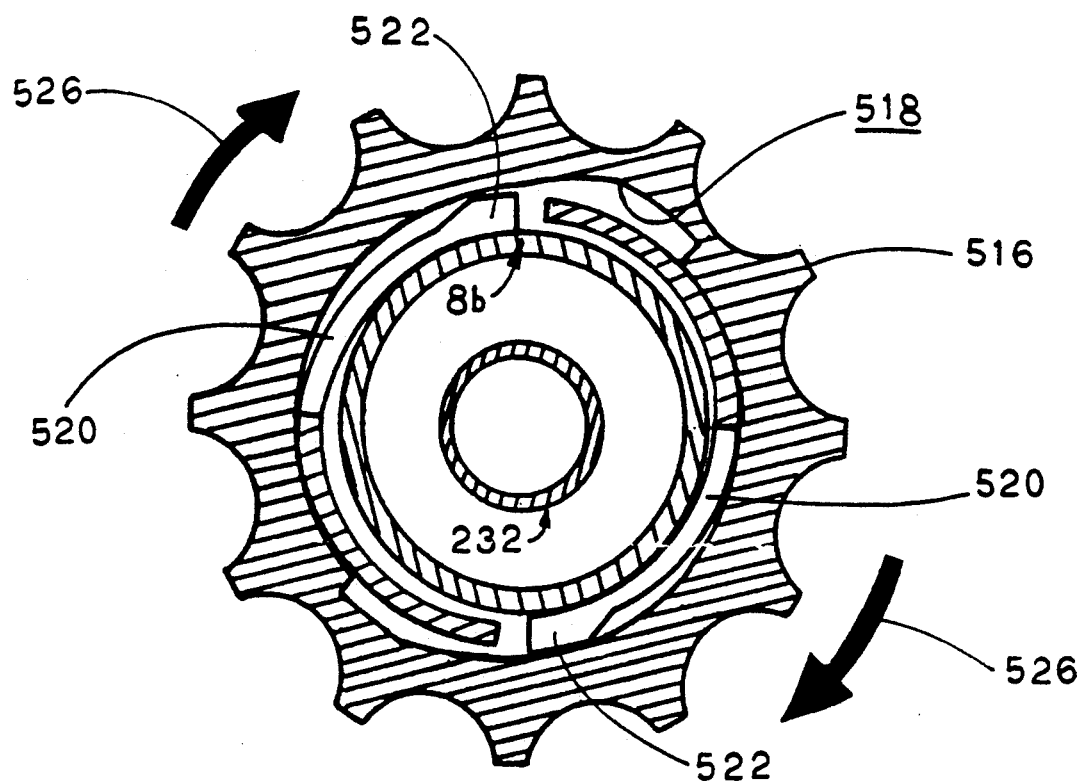

FIGS. 12-15 relate to a further embodiment of the invention in which the distal portion, shown in FIG. 9A, of instrument 2b, shown in FIGS. 13A and 13B, has been modified. The purposes for the modifications are to permit the user to selectively lockout or prevent rotary motion of the jaws relative to the base and also to permit the user to easily and quickly replace one tip assembly with another tip assembly. Many of the elements are the same as or similar to those described above; these elements will not be described in detail but will be referred to with like reference numerals.

Tip carrier tube 8b is similar to tip carrier tube 8a but lacks internal threads 154 and has a circular hole 502 instead of slot 314. The purpose of hole 502 will be described below. Base extension 504 is secured to base 6b (see FIG. 14) and acts as an extension of base 6b. Base extension 504 includes an elongate cylindrical portion 506 and a bearing end 508. Bearing end 508 has internal threads 510 which engage external threads 512 formed at the distal end of base 6b. Accordingly, base extension 504 is a one piece, rigid extension of base 6b and thus does not rotate or move axially relative to the base. Bearing end 508 also helps to capture a set of ball bearings 162 between an internal shoulder 514 formed at bearing end 508 and annular shoulder 66a formed as a part of tip carrier tube 8b.

Due to the presence of sets of ball bearings 160, 162, tip carrier tube 8b can rotate relative to base 6b and base extension 504. This relative rotary motion can be prevented through the use of a serrated lockout collar 516. Serrated lockout collar 516 has a pair of internal cam surfaces 518 which lie opposite a pair of resilient lockout fingers 520. Lockout fingers 520 have cam bumps 522 formed at their distal ends which engage internal cam surfaces 518. Collar 516 is held in a fixed position axially along base extension 504 by a retainer band 524 which is press fit over cylindrical portion 506 of base extension 504. When lockout collar 516 is at the free movement position of FIG. 15A, lockout fingers 520 are spaced apart from tip carrier tube 8b so that tip carrier tube 8b can move freely within base extension 504. However, rotating lockout collar 516 in the direction of arrows 526 to the rotary motion lockout position of FIG. 15B causes lockout fingers 520 to press tightly against tip carrier tube 8b, thus frictionally securing the tip carrier tube to base extension 504 and thus to base 6b.

Axial drive 232 has a flanged drawbar 258a mounted to its distal end 263 by capturing flange 260 between sets of ball bearings 264, 266. Drawbar retaining nut 268 passes over flanged drawbar 258a and is threadably secured to the threads at end 263.

The distal end 530 of flanged drawbar 258a has a lateral hole 532 formed therethrough. Hole 532 is sized to accept a pin 534 to permit distal end 530 to be secured to the proximal end 536 of a bayonet receptacle 538. Receptacle 538 is a generally cylindrical member having a laterally extending hole 540 at its proximal end 536 sized for receipt of pin 534. Bayonet receptacle 538 has a pair of L-shaped slots 542. These L-shaped slots are used for engaging the tip assembly 10b as is discussed below.

Tip assembly 10b includes the rest of the structure shown in FIG. 12 and not yet discussed. Tip assembly 106 includes a tip tube 544 having an internally threaded distal end 546 to which tip coupler plug 148 is threadably secured. Tip assembly 10b also includes a fork 292a which is mounted to the interior of tip tube 544 through a press fit. Fork 292s is sized so that the proximal end 548 of fork 292a extends past proximal end 550 of tip tube 544. Fork 292a includes an axially extending slot 552 sized to accept a generally Z-shaped catch spring 554. The proximal end 556 of catch spring 554 is a radially extending tip which extends out past the outside surface of tip tube 544. The proximal end 548 of fork 292a is sized to fit within tip carrier tube 8b so that proximal end 556 of catch spring 554 can engage hole 502 formed in the tip carrier tube. Doing so retains tip tube 544 and fork 292a therewith in position both axially and radially relative to tip carrier tube 8b.

As discussed above, cam block 280a is mounted within wider gap 296a of fork 292a. Cam block 280a includes a cam block extension 558 which passes through and is guided by an internal shoulder 560 (see FIG. 13) formed within fork 292a. A bayonet pin 562 passes thorough a lateral bore 564 formed in the proximal end 566 of guide block extension 558. Pin 562 engages L-shaped slots 542 to permit tip assembly 10b to mounted to and disengaged from the remainder of the instrument.

Tip assembly 10b includes broadly tip tube 544, fork 292a, Cam block 280a, tip coupler plug 148 and jaws 28a, 28b. To mount an appropriate tip assembly 10b to the remainder of instrument 2b, the user inserts cam block extension 558 and proximal end 548 of fork 292a through the distal end 12b of tip carrier tube 8b until bayonet pin 562 contacts bayonet receptacle 538. Bayonet receptacle 538 is held in place by flanged drawbar 258a. The user then rotates tip assembly 10b until bayonet pin 562 becomes aligned with the axially extending portions of slots 542. The user than pushes tip assembly 10b axially and then twists the tip assembly until bayonet pins 562 engage the circumferentially extending portions of slots 542. When this occurs proximal end 556 of catch spring 554 becomes aligned with and moves into hole 502 thus securing tip assembly 10b in place. When it is desired to replace tip assembly 10b, for example if a different type of jaws 28a, 28b is needed, the user inserts a tool into hole 502 to depress proximal end 556 of catch spring 554. The user then rotates tip assembly 10b to align bayonet pin 562 with the axially extending portions of slots 542 and then pulls tip assembly 10b out of tip carrier tube 8b. The replacement tip assembly can then be mounted within tip carrier tube 8b. If during use the user desires to prevent tip assembly 10b from rotating relative to base 6b, the user merely rotates lockout collar 516 in the direction of arrows 526.

Figure 9B:
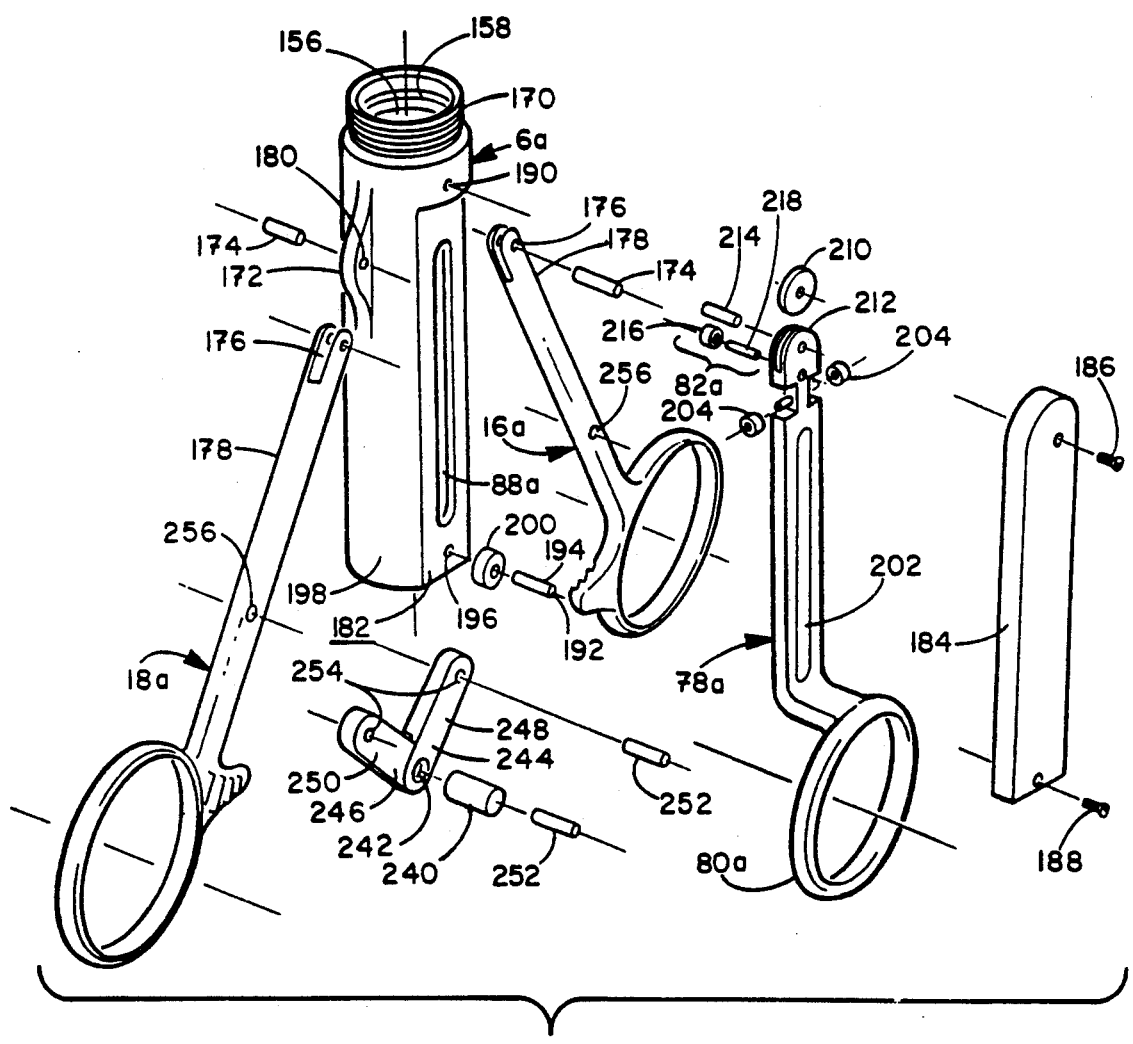

Other types of mechanisms can be used to keep tip carrier tube 8b from rotating relative to base 6b. Various types of clamps or thumbscrews could be used. With reference to FIG. 9B, rotary actuator trigger 78a could have a serrated surface along its length and base 6a could include some type of catch or keeper along slot 88a which could be actuated to engage the serrated surface along trigger 78a, thus locking the trigger in place.

Other modification and variation can be made to the disclosed embodiments without departing from the subject of the invention as defined in the following claims. For example, other methods for mounting a tip assembly to the remainder of the device could be used as well. It may be desired to spring bias loops 16, 18 away from one another and trigger 78 towards the position of FIG. 1.

What is claimed is:

1. An improved endoscopic surgical instrument comprising:
   a body having a distal end and a proximal end;
   a tip assembly mounted to the body, the tip assembly including at least one movable tip element;
   a tip element driver assembly including a user manipulative movable tip element actuator, movably mounted to the proximal end of the body, and a driver assembly coupling the movable tip element actuator to at least the movable tip element, so that when the user manipulates the movable tip element actuator the movable tip element moves relative to the body;
   a tip assembly rotator including a user manipulatable rotary actuator, movably mounted to the proximal end of the body, and a rotary driver, drivingly coupling the rotary actuator and the tip assembly, so that user manipulation of the rotary actuator causes at least the movable tip element to rotate; and
   means for selectively increasing and decreasing resistance to relative rotary motion between the tip assembly and the body.

2. The instrument of claim 1 wherein the movable tip element is a movable first jaw, the tip assembly includes a second jaw fixed to the body and the first jaw moves relative to the body and the second jaw.

3. The instrument of claim 1 wherein the tip element actuator includes jaw actuating finger and thumb elements pivotally mounted to the body and drivingly coupled together.

4. The instrument of claim 3 wherein the body defines an axis passing through the distal and proximal ends and the finger and thumb elements are positioned on opposite sides of the axis.

5. The instrument of claim 4 wherein the axial driver assembly includes drive linkage segments and an axial drive tube having a proximal end coupled to the drive linkage segments.

6. The instrument of claim 1 wherein the rotary driver is drivingly coupled to the tip assembly so manipulation of the rotary actuator causes the tip assembly to rotate.

7. The instrument of claim 6 wherein the body includes a base, and a tip carrier tube rotatably mounted to the base, the tip assembly mounted to the base through the tip carrier tube.

8. The instrument of claim 7 wherein the rotary actuator includes a rotary actuator finger element slidably mounted to the base and the tip carrier tube includes a spiral groove, the rotary actuator finger element having a cam pin slidably engaging the spiral groove so that linear movement of the rotary actuator finger element causes the cam pin to move along the spiral groove formed in the tip carrier tube, thereby rotating the tip carrier tube and the tip assembly therewith.

9. The instrument of claim 8 wherein the tip assembly is removably mounted to the tip carrier tube.

10. The instrument of claim 9 wherein the tip assembly is mounted to the tip carrier tube by a threaded tip coupler plug.

11. The instrument of claim 1 wherein the tip assembly is removably mounted to the body.

12. An endoscopic surgical instrument comprising:
    a body having distal and proximal ends and defining a longitudinal axis therebetween;
    at least one movable tip element mounted to the body for movement relative to the body;
    user actuated means for moving the at least one tip element relative to the body;
    user actuated means for rotating the at least one tip element about the longitudinal axis of the body; and
    means for selectively increasing and decreasing resistance to relative rotary motion between the at least one movable tip element and the body.

13. The instrument of claim 12 further comprising means for removably mounting the at least one movable tip element to the body.

14. The instrument of claim 12 wherein the at least one movable tip element is part of a tip assembly, and further comprising means for removably mounting the tip assembly to the body.

15. An improved endoscopic surgical instrument comprising:
    a body having distal and proximal ends;
    a tip assembly mounted to the body and including at least one movable tip element;
    a tip element driver assembly including a user manipulatable tip element actuator, movably mounted to the proximal end of the body, and a driver assembly coupling the movable tip element actuator to at least the movable tip element, so that when the user manipulates the movable tip element actuator the movable tip element moves relative to the body;
    a tip assembly rotator including a user manipulatable rotary actuator, movably mounted to the proximal end of the body, and a rotary driver, drivingly coupling the rotary actuator and the tip assembly, so that user manipulation of the rotary actuator causes at least the movable tip element to rotate;
    the tip element actuator including jaw actuating finger and thumb elements pivotally mounted to the body, the body defining an axis passing through the distal and proximal ends and the finger and thumb elements being positioned on opposite sides of the axis;
    means for selectively preventing relative rotary motion between the tip assembly and the body; and
    the driver assembly including drive linkage segments, an axial drive tube having a proximal end coupled to the drive linkage segments, and a cam member secured to the axial drive tube for axial movement therewith, the cam member including a cam slot, the movable tip element engaging the cam slot so that axial movement of the cam member causes the movable tip element to move laterally.

16. An endoscopic surgical instrument comprising:
a body having a distal end and a proximal end;
a tip assembly removably mounted to the distal end of the body;
the tip assembly including at least one movable tip element, the movable tip element being movable relative to the body;
a tip element driver assembly including a user manipulatable tip element actuator, movably mounted to the proximal end of the body, and a driver assembly coupling the movable tip element actuator to the at least one movable tip element, so that when the user manipulates the movable tip element actuator the movable tip element moves relative to the body;
the tip element actuator including tip element actuating finger and thumb elements pivotally mounted to the body and drivingly coupled together, the body defining an axis passing through the distal and proximal ends; and
a tip assembly rotator including a user manipulatable rotary actuator, movably mounted to the proximal end of the body, and a rotary driver, drivingly coupling the rotary actuator and the tip assembly, so that user manipulation of the rotary actuator causes the tip assembly to rotate.

17. An endoscopic medical instrument comprising:
a body having distal and proximal ends defining a longitudinal axis therebetween;
a tip assembly removably mounted to the body;
the tip assembly including first and second jaws, at least the first jaw being movable relative to the second jaw between open and closed jaw positions;
user actuated means for moving at least the first jaw between the open and closed jaw positions;
the moving means including jaw actuating finger and thumb elements movably mounted to the body;
user actuated means for rotating the jaws about the longitudinal axis of the body;
user actuated means for selectively increasing and decreasing resistance to relative rotary motion between the tip assembly and the body; and
means for removably mounting the tip assembly to the body so to permit removal and replacement of one said tip assembly with another tip assembly.

18. An endoscopic surgical instrument comprising:
a body having distal and proximal ends and a longitudinal axis therebetween;
a tip assembly mounted to the body, the tip assembly including a tip coupler plug and at least one movable tip element movably mounted to the tip coupler plug for movement relative to the tip coupler plug and the body;
user actuated means for moving the at least one tip element relative to the body;
user actuated means for rotating the at least one movable tip element about the longitudinal axis of the body, the rotating means being connected to the tip coupler plug; and
means for manually removably mounting the tip assembly to and dismounting the tip assembly from the rotating means.

19. An improved endoscopic surgical instrument comprising:
a body having distal and proximal ends;
a tip assembly mounted to the body and including at least one movable tip element;
a tip element driver assembly including a user manipulatable tip element actuator, movably mounted to the proximal end of the body, and a driver assembly coupling the movable tip element actuator to at least the movable tip element, so that when the user manipulates the movable tip element actuator the movable tip element moves relative to the body;
a tip assembly rotator including a user manipulatable rotary actuator, movably mounted to the proximal end of the body, and a rotary driver, drivingly coupling the rotary actuator and the tip assembly, so that user manipulation of the rotary actuator causes the tip assembly to rotate;
a body tubular element fixed to the body;
the rotary driver including a rotatable tubular element at least partially housed within the body tuber element and rotatably coupled to the tip assembly for coextensive rotary motion therewith;
a user actuated locking device carried by the body tubular element by which the body tubular element is secured to the rotatable tubular element so as to prevent relative rotary motion therebetween, the user actuated locking device including:
a lockout collar mounted over the body tubular element;
a lockout finger formed as an integral part of the body tubular element; and
cam means, acting between the lockout collar and the lockout finger, for biasing the lockout finger against the rotatable tubular element thereby fictionally securing the tubular body element to the rotatable tubular element so to prevent relative rotary motion therebetween.

20. An improved endoscopic surgical instrument comprising:
a body having a distal end and a proximal end;
a tip assembly mounted to the body, the tip assembly including first and second jaws, the first jaw being movable relative to the second jaw;
a jaw driver assembly including a user manipulatable jaw actuator, movably mounted to the proximal end of the body, and a driver assembly coupling the movable jaw actuator to at least the first jaw, so that when the user manipulates the movable jaw actuator the first jaw moves relative to the body;
a tip assembly rotator including a user manipulatable rotary actuator, movably mounted to the proximal end of the body, and a rotary driver, drivingly coupling the rotary actuator and the tip assembly, so that user manipulation of the rotary actuator causes at least the first jaw to rotate;
means for manually removably mounting the tip assembly to and removing the tip assembly from the body.

21. An improved endoscopic surgical instrument comprising:
a body having a distal end, a proximal end, a base, and a tip carrier tube rotatably mounted to the base;
a tip assembly mounted to the body, the tip assembly including at least one movable tip element, the tip assembly being mounted to the tip carrier tube by a threaded tip coupler plug;
a tip element driver assembly including a user manipulatable movable tip element actuator, movably mounted to the proximal end of the body, and a driver assembly coupling the movable tip element actuator to at least the movable tip element, so that when the user manipulates the movable tip element actuator the movable tip element moves relative to the body;

a tip assembly rotator including a user manipulatable rotary actuator, movably mounted to the proximal end of the body, and a rotary driver, drivingly coupling the rotary actuator and the tip assembly, so that user manipulation of the rotary actuator causes at least the movable tip element to rotate; and means for selectively increasing the decreasing resistance to relative rotary motion between the tip assembly and the body.

* * * * *